US012622375B2

(12) United States Patent
Markosyan et al.

(10) Patent No.: US 12,622,375 B2
(45) Date of Patent: May 12, 2026

(54) HIGH REBAUDIOSIDE M STEVIA PLANT CULTIVARS AND METHODS OF PRODUCING THE SAME

(71) Applicants:PureCircle USA Inc., Chicago, IL (US); KeyGene N.V., Wageningen (NL); The Coca-Cola Company, Atlanta, GA (US)

(72) Inventors: Avetik Markosyan, Yerevan (AM); Seong Siang Ong, Bandar Enstek (MY); Runchun Jing, Ganzhou City (CN); Tengfang Huang, Cary, NC (US); Fayaz Khazi, Chapel Hill, NC (US); Stephen Ezra Schauer, Rockville, MD (US); Indra Prakash, Alpharetta, GA (US); Alec Hayes, Marietta, GA (US)

(73) Assignees: PureCircle USA, Inc., Westchester, IL (US); KeyGene N.V., Wageningen (NL); The Coca-Cola Company, Atlanta, GA (US)

( * ) Notice: Subject to any disclaimer, the term of this patent is extended or adjusted under 35 U.S.C. 154(b) by 284 days.

(21) Appl. No.: 18/538,856

(22) Filed: Dec. 13, 2023

(65) Prior Publication Data

US 2024/0138331 A1     May 2, 2024

Related U.S. Application Data

(62) Division of application No. 17/701,154, filed on Mar. 22, 2022, now Pat. No. 11,844,323, which is a division of application No. 16/491,470, filed as application No. PCT/US2018/021389 on Mar. 7, 2018, now Pat. No. 11,284,577.

(60) Provisional application No. 62/468,937, filed on Mar. 8, 2017.

(51) Int. Cl.
*A01H 6/14*          (2018.01)
*C12N 15/82*         (2006.01)

(52) U.S. Cl.
CPC ....... *A01H 6/1488* (2018.05); *C12N 15/8245* (2013.01); *C12N 15/8279* (2013.01)

(58) Field of Classification Search
CPC .......................... A01H 6/1488; C12N 15/8245
See application file for complete search history.

(56) References Cited

U.S. PATENT DOCUMENTS

| | | | |
|---|---|---|---|
| 7,927,851 B2 | 4/2011 | Brandle | |
| 8,703,225 B2 | 4/2014 | Morita | |
| 9,668,451 B2 | 6/2017 | Li et al. | |
| 10,370,673 B2 | 8/2019 | Markosyan et al. | |
| 11,284,577 B2 | 3/2022 | Markosyan et al. | |
| 11,844,323 B2 | 12/2023 | Markosyan et al. | |
| 2014/0329281 A1 | 11/2014 | Houghton-Larsen et al. | |
| 2016/0057965 A1* | 3/2016 | Li ............................ | A01H 5/02 |
| | | | 800/300 |
| 2016/0057966 A1 | 3/2016 | Li et al. | |
| 2016/0058052 A1 | 3/2016 | Markosyan et al. | |
| 2016/0198748 A1 | 7/2016 | Prakash et al. | |
| 2016/0288159 A1 | 10/2016 | Tao et al. | |
| 2020/0095597 A1 | 3/2020 | Markosyan et al. | |
| 2022/0210992 A1 | 7/2022 | Markosyan et al. | |

FOREIGN PATENT DOCUMENTS

| | | |
|---|---|---|
| AP | 5634 A | 6/2021 |
| AR | 111187 A1 | 6/2019 |
| IN | 201917037420 A | 11/2019 |
| WO | 2016049531 A1 | 3/2016 |
| WO | 2016130609 A1 | 8/2016 |
| WO | 2018165330 A1 | 9/2018 |

OTHER PUBLICATIONS

Amendment for U.S. Appl. No. 17/701,154 (now U.S. Pat. No. 11,844,323), submitted May 16, 2023, 12 pages.
Communication under Rules 70(2) and 70a(2) EPC for European Patent Application No. 18764962.9 mailed Nov. 12, 2020, 1 page.
Decision on Rejection for China Application No. 201880016402.7 with English translation mailed on Sep. 21, 2022, 11 pages.
Decision to Grant and Search Report for African Regional Intellectual Property Organization (ARIPO) Application No. APP2019011829 mailed Feb. 19, 2022, 6 pages.
Examination Report for European Application No. 18764962.9, mailed Aug. 12, 2021, 6 pages.
Extended European Search Re ort for European Patent Application No. 18764962.9 mailed Oct. 26, 2020, 9 pages.
International Search Report and Written Opinion for International Application No. PCT/US2018/021389, Jun. 18, 2018, 7 pages.
Non-Final Office Action for U.S. Appl. No. 17/701,154 (now U.S. Pat. No. 11,844,323), mailed Feb. 16, 2023, 13 pages.
Non-Final Office Action received for U.S. Appl. No. 16/491,470 (now U.S. Pat. No. 11,284,577), mailed Jun. 10, 2021, 29 pages.
Notice of Allowance and Examiner Interview for U.S. Appl. No. 16/491,470 (now U.S. Pat. No. 11,284,577), mailed Nov. 23, 2021, 15 pages.
Notice of Allowance for U.S. Appl. No. 17/701,154 (now U.S. Pat. No. 11,844,323), mailed Sep. 7, 2023, 8 pages.
Office Action for Argentine Application No. P 18 01 00541 malled on Mar. 17, 2022, 5 pages.
Office Action for China Application No. 201880016402.7 with English translation mailed on Dec. 22, 2021, 17 pages.

(Continued)

*Primary Examiner* — David H Kruse
(74) *Attorney, Agent, or Firm* — Weatherly IP Solutions, LLC; James M. Weatherly

(57)          ABSTRACT

*Stevia* varieties with a high content of RebM, are disclosed Further provided are methods for producing *Stevia* plants having a high RebM content by negatively regulating certain genes selecting the resulting plants, and breeding with such plants to confer such desirable Reb M phenotypes to plant progeny.

5 Claims, 1 Drawing Sheet

Specification includes a Sequence Listing.

(56)          References Cited

OTHER PUBLICATIONS

Prakash et al., "Isolation and characterization of a novel rebaudioside M isomer from a bioconversion reaction of rebaudioside A and NMR comparison studies of rebaudioside M isolated from Stevia rebaudiana Bartoni and Stevia rebaudiana Morita", Biomolecules, (Mar. 31, 2014), vol. 4, doi:doi:10.3390/biom4020374, pp. 374-389, XP055237016.

Prakash, Indra, et al., "Development of Next Generation Stevia Sweetner: Rebaudioside M," XP55737952, Foods, vol. 3, No. 1, pp. 162-175 (Jan. 1, 2014).

Response to Communication Under Rules 161(2) and 162 EPC for European Patent Application No. 18764982.9 submitted Apr. 27, 2020, 3 pages.

Response to Examination Report or European 18764962.9, filed on Feb. 21, 2022, 6 pages.

Response to Extended European Search Report and Communication under Rules 70(2) and 70a(2) EPC with amended claims for European Patent Application No. 18784962.9 submitted May 18, 2021, 5 pages.

Response to Non-Final Office Action for U.S. Appl. No. 16/491,470 (now U.S. Pat. No. 11,284,677), filed Sep. 10, 2021, 12 pages.

Response to Office Action for Argentine Application No. P 18 01 00541 filed on Jun. 29, 2022, 5 pages.

Response to Office Action or China Application No. 201880016402.7, filed Jul. 6, 2022, 140 pages.

Response to Restriction Requirement for U.S. Appl. No. 16/491,470 (now U.S. Pat. No. 11,284,577), filed Mar. 15, 2021, 3 pages.

Restriction Requirement for U.S. Appl. No. 16/491,470 (now U.S. Pat. No. 11,284,577), mailed Dec. 15, 2020, 7 pages.

Yadav, Ashok Kumar, et al., "A review of the improvement of stevia [*Stevia rebaudiana* (Bertoni)]," XP055550835, Canadian Journal of Plant Science, vol. 91, No. 1, pp. 1-27 (Jan. 1, 2011).

* cited by examiner

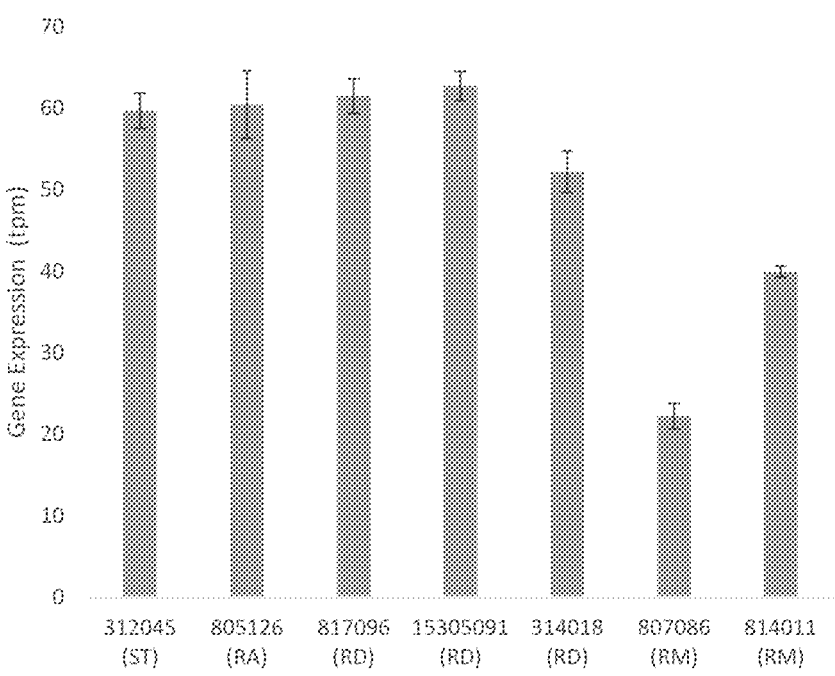

SEQUENCE LISTING

```
Sequence total quantity: 20
SEQ ID NO: 1              moltype = DNA   length = 717
FEATURE                  Location/Qualifiers
source                   1..717
```

```
                                mol_type = genomic DNA
                                organism = Stevia rebaudiana
SEQUENCE: 1
atgttaggtc cccagtgctg caaaaatcca ccggcaatca gctccggtag ccaacaaaag   60
gatcacatag aagtaatcgg aggcttaaca tcatacacta ccggcaccct tgattctaag   120
cttgctgtca tttttgattgc tgacatattt ggctatgaat ccccaaaact aagacaaatt   180
gctgacaaag ttgcagcagc tggatttat gtagttgtgc ctgatttctt ttatggagat    240
ccttatttac ctcacatgac aataccttca tggtatccta atcatcaacc ggaaaaaggg    300
tgtgaagatg ccagaaaggt agttgctgat ttgaaaagaa aaggagcaac tgcaattgga    360
gttgccggtt tctgttgggg aggtatgttt ttgtcaaaac tgtcgagtta tggtgagatt    420
gatgttgctg ttgtactaca ccctggtcgg ctaacagaag atgatattca agaaacaaaa    480
gtcccaacag caatcttagg tgctgaattt gatgagcatg ctccacctga acaaatgaaa    540
aaattggggg aaattttaac agaaaaatca atagataatt ttgtgaagat atacccctgga   600
gttgatcatg gttggacaac aagatacaaa gatgatgatg aacatgatgt taaaaccgca    660
atggaagcac atgaggacat gttaaattgg cttaaaaaat atcttaaaca aaaatga       717

SEQ ID NO: 2                    moltype = DNA   length = 1512
FEATURE                         Location/Qualifiers
source                          1..1512
                                mol_type = genomic DNA
                                organism = Stevia rebaudiana
SEQUENCE: 2
atgagtggac ctgcatcgga tgatcttcaa ccggaaaccg gttgtctttc agttattgtt    60
ctcggggctt ccggtgatct agccaagaaa aagacgtttc ctgcactctt tcatcttcat    120
cgtcaaggat tcattgcatc acatgatgtc cgtattttcg gttatgcaag aagtaaactg    180
tcggatcaag atttgcgaca ccaacttcgt agatatttga caccatgcaa aggttgtgaa    240
gaaacacacg aggaagatgt atcaaagttt cttcaattga tcaaatatat aagcggcgcg    300
tatgatgctg aggagggatt ccggtcacta aatgatgaaa tatccgcaca cgaaaggtca    360
aaaggcgaca aaggaggacc atacaaaaga ctcttctact ttgcacttcc tccgtccata    420
tatccacccg tttgtaaaat gataaaatgt tgttgcatga gcaaatccga aggtggttgg    480
acacgcgttg ttgttgagaa accttttggc aaagatctga gttcatctga agcattgagt    540
aagcagatag gagaattgtt tgatgaatca caaatctacc gtatcgatca ttacttgggg    600
aaagagttgg tgcagaatct gttggtgtta cgttttgcta atcgattttt cttgccattg    660
tggaaccatg ataatatttc aactgtacag attgtattta aagaggattt tggaactgaa    720
ggtcgtggcg gatatttaa tgaatatgga attattaggg acatacttca aaatcattta     780
ctacaggtgc tttgtttggt tgcaatggag aaacctgttt ctttaaaacc tgaacatatt    840
cgagatgaga aagtgaaggt tctacaatct gttctacaga tcaaagatga tgaagttgtg    900
attggacaat atgaaggcta tacgaatgat cccactgttc ctaaagaatc aaacactccc    960
actttgcaa caatggtttt aagaattcac aatgaaagat gaggaggtgt tccgtttata    1020
ttgaaagctg gaaaatcaat gaattcaaaa aaagctgaga ttagaatcca atttaaagat   1080
gttcctggtg atatattcac ttcaaagggc aaagggagaa atgagtttgt cattcgattg    1140
caaccttcag aagccattta catgaagcta actgtcaagg agcctgggct ggagatgaaa   1200
actgctcaaa gtgaactaga cttatcatat cgccaaagat aacaagaagt cgttatccca   1260
gaagcatacg aacgtctgat acttgacact attcggggtg atcaacaaca ttttgttcgt   1320
agagatgaac taaaggccgc ttgggagatc tttaccccat tgttgcacaa aatagataac   1380
aacgaaatgc gatcacttcc atataagcca ggaagccggg gccagagga tgcagataag    1440
ttggctaaaa aggtaggata cgttcaaacc cacggatacg tatggatccc accaacatta    1500
agcgcggttt ag                                                       1512

SEQ ID NO: 3                    moltype = DNA   length = 1521
FEATURE                         Location/Qualifiers
source                          1..1521
                                mol_type = genomic DNA
                                organism = Stevia rebaudiana
SEQUENCE: 3
atgaatctgt atatatccag gggattaatc tcttcaatct ttcatcaaac tatcttatgt    60
tttctagcca tggttttttct aattttattg ttattactga ttttggttcc aatctttttc   120
cttttccatc ataataacaa gcataatcgc caactaccac ctggttcttt aggacttccg    180
gtaattgggc aaagcatcgg cctttttgaag gccttgaagg ccgacaggt cgagaaatga    240
tttcacgaaa gaataacaaa gcacggtccg gtttggaaga cgagtctttt tggatacccg    300
acggttgtct tgcatggtcc aaccgcgaat aagttcatat acacttgtga cgggaataca    360
cttaccccca cacaaccatc gtcagtcagt aggatcttgg gttccaaaaa tttattagag    420
ttgtcgggca atgatcacaa acgagtcaga tcggctctag tttcgtttct taagcttgaa   480
gtgttgaaac aatatgttgc aaaagtagat gaagaggtcc aacatcacct tctaacccat    540
tggcatggta aacatgaggt ccaggtacaa ccccttatca agatcttaac cttcaacgtc    600
atttgttcgc ttttgtttgg gattgaaaga ggacccaaac gagataattt gctaccactt    660
ttccaagata taattgaagg ggtgttgtca attccaatca atttgccttt cactcaattt    720
aggcgtggta ttatagcaag gaagaaactt gtaccaatga tttcacatat catacgtgag    780
aaaagagagg tcttaagga acaaaatcaa caaattgact cacataaaga tctaatcaca    840
tcattactta acatttgtga tgatgatggc tcaaaaatta tgtccgaaga tgagatcatt    900
gacaacatca tcattgtgat ggttgcagga tatgacacca cctctgttct tcttaccttc    960
ttggtcaggc ttttggctaa caataaatct atctactctg ctatagttca agaacaacaa   1020
gaaattgcca ataaaaagt gtctgaagaa gctttaacat gggaagacct tgcaaagatg   1080
aagtacacat ggaggatagc aactgagatg ttgcggatta cccacctgt gactttgagc    1140
ttccgacgtg ctaagcaaga tatcacgtat gaaggatttg taattccaaa aggatggcaa   1200
gtgatgttat cggcatccat gacacatagg gatgatagca ttttcaaaaa tccaaccata   1260
tttgatccaa ctcgtttttga gaaacatgca ccatcgccac caccatttag ttttgtggca   1320
tttgaggcg ggccaaggat gtgtcctggt attgagcttg caaaaatgga aactttaatc    1380
atgatgcatc gtctcgtgac aagattctct tgggagctac ttgagaaaga tgaatccttc    1440
```

```
aagagggttc cattgccaga atttgatcaa gggttgttag ttcaggtgaa gccttttaaaa   1500
ggaagccatg aaggtatgtg a                                              1521

SEQ ID NO: 4              moltype = DNA  length = 1599
FEATURE                   Location/Qualifiers
source                    1..1599
                          mol_type = genomic DNA
                          organism = Stevia rebaudiana
SEQUENCE: 4
tccgatctat cagattttag agataagatc tatctcacta tcatcaacaa ctggtcatgg    60
tggtgtaaag tagacaatga aaaagacaag ctttctcgca ccatcctcac catcttagtt   120
ccggttctag tccttgtatg gttcaagtgg acccaatcgt ttatccgaaa tggaaaaaac   180
ccgttaccac caggcccta tggcttaccg gtcgtcggtt accttccgtt tttgagccca    240
aacttacacg aaagattcac cgagatggct caccgatacg gtcctatctt tagcctaagg   300
ctcggaagta agttacatgt tgtggtgaac aacatggagc tagcaaaggt tgtggctcgt   360
gatcttgacc agacctttgc taaccgtagt ccaccgatga cagcactaac catcagttat   420
ggcgcgcttg atatcgcgtg gtccaacaac aacgcgcact ggcgtaacat gcgtaagctt   480
ttagtgagcc aagtgttgag caatgcgaat cttgatgcgt gtcaaggttt tagaataaat   540
gaagtcagaa aaaccgttaa taacgtttat gcaaaaatgg ggacaccagt tgatatcaat   600
caaattgcat tcgacacgga acttaacgtt gtaatgaaca tgttatgggg ttgtagtaat   660
gattctggtg attattttca gggggtttcga gaagttgagt tcaagattat agatttattg   720
ggtgtaccaa atatctctga tttatcccg atgttatcat ggtttgattt gcagggaaga    780
aagaaagata tgcagaagca aaaggaacat cttgatcgga ttttggacca cgtaattgaa   840
gaaagaattg aaagaaactc gagaaaaatg gagggtgagg atgatcgtaa caaggatttt   900
ttgcagatca tgttagagct taaagatcag aaagatggtt catcatcatt tgacatagtt   960
catataaaag ccatgttatt tgacatcttg acagcaacaa cagacacagc atcaacaatg  1020
gtagaatggg tgatggcaga gattttgcat aatccagatg taaaaacaaa gattcaagaa  1080
gaattaaccg aggttatcgg tatggatatt gttcaagaat ctcatctacc caaattaata  1140
tatttggatg cagtagtcaa agagacattc agactacatc ctcccacttcc actcttaatc  1200
caaagatgcc cggatgaaac ttgcattgtg gacggatacg cgattccaaa gggtagtatc  1260
gtctatataa atgttcgggc tacaacacac gatccaaaga actggcccga tccattggag  1320
tttaggcccg agagattctt gaaaggaaaa tgggattaca atggaaataa tttgaagttt  1380
ttaccgtttg gatcaggaag aagaatttgt cctggaatcc ctttagggga gaagatgttg  1440
atgtatatat tagcatcact tttgcattct tttgagtgga tcttgcataa agatgaagag  1500
tttgagcttt cagatgagtt tggatttgta accaagaaac ggaaaccact ggttgcaatt  1560
ccttttcaaa gattatcaga tgaaaccctc tacaaatga                          1599

SEQ ID NO: 5              moltype = DNA  length = 1431
FEATURE                   Location/Qualifiers
source                    1..1431
                          mol_type = genomic DNA
                          organism = Stevia rebaudiana
SEQUENCE: 5
atgattcaag ttctaacacc gatccttctc ttcctcattt tcttcgtttt ctggaaggtt    60
tacaagcacc acaaaaccaa aatcaatctt ccaccgggaa gcttcggatg gccatttctg   120
ggcgaaactc tggcactcct acgtgcaggt tgggattcag agccggagag atttgttcgt   180
gaacggatca agaaacacgg aagtcctcta gtgtttaaga cgtcgttgtt tggcgaccgt   240
tttgcggtgt tgtgtggacc tgccggaaac aagttcctgt tctgcaacga gaacaagctg   300
gtggcgtcgt ggtggccggt tccggtgagg aagcttttcg gcaagtctct gctcacgatt   360
cgtggtgatg aagctaagtg gatgaggaag atgttgttat cgtatcttgg tcctgatgct   420
ttcgcaactc attatgccgt cacaatggac gtcgtcaccc gtcggcatat cgacgttcat   480
tggcgaggga aggaagaggt gaacgtattc caaaccgtta agttatatgc ctttgaactt   540
gcatgtcgtt tattcatgaa cctagacgac ccaaaccaca ttgcaaaact cggttccttg   600
ttcaaaattt tcttgaaagg catcattgag cttccaatcg acgtcccagg gacacggattt  660
tatagcgcca aaaaagcagg agcagctatc aggattgaac taaaaaaatt gattaaagca   720
agaaaactgg aactgaaaga agggaaggca tcatcttcac aagacctctt atcacatttg   780
cttacatctt cagatgaaaa tggtatgtt ctaaccgaag aagagattgt agacaacatc    840
ttgttactac tctttgcggg tcatgatacc tcggctcttt caatcactt gctcatgaag    900
actcttggcg aacattctga tgtttatgac aaggtgtaa aagagcaact agagatctct    960
aagacgaaag aagcatggga atcactgaaa tgggaggaca tacaaaagat gaaatactcc   1020
tggagtgttg tatgtgaagt catgagacta aatccaccg ttataggaac ctatagagag   1080
gcccttgtgg atatcgagta tgctggttat accatcccca aaggatggaa gctacactgg   1140
agtgctgtat cgacacaaag ggacgaggct aatttgaag gcgtaacacg ttttgaccca    1200
tcacggtttg aaggcgcagg accgactcca ttcacctttg ttccgtttgg agggggggcct  1260
aggatgtgtt tagggaaaga atttgctcga ttggaagtgc ttgcgtttct tcacaatatt   1320
gtcaccaatt tcaaatggga cctgttgata cctgatgaga aaatagaata tgatcccatg   1380
gctaccccag caaaggggct tccaattcgt cttcatcccc atcaagtttg a            1431

SEQ ID NO: 6              moltype = DNA  length = 1638
FEATURE                   Location/Qualifiers
source                    1..1638
                          mol_type = genomic DNA
                          organism = Stevia rebaudiana
SEQUENCE: 6
atggcatcca accaagagga ggttattcga cccgtggcaa attttcatcc cagcctttgg    60
ggagataaat tcttatcta tcaagagctg gaagaacagg atgtgataga acgaacaatc    120
aacggtctga aaaatgaatt gaggatagaa ctatcgtctg ctttgaacga tccagcacaa   180
catagaaatt tgttgaaact tattgataat attcaacgcc taggcatagc ttactacttc   240
gaaaacaata ttgatgaagc attgcaacat atttataata tatatggtga cgactggaaa   300
```

```
ggtcataaca cgcctctttg gttccgactc ctccgacaac aaggctttta tgtttccacc  360
gatggtctta acaagtataa gcccggtaaa aaagtggaat tcttaaccga tgatgttcaa  420
gggttgcttg acttgtacga ggccatgtat atgagggtgc caggcgaaga attactagat  480
gatgctctta tttgtattaa aactcgtctt ggtagcatag caaatgatcc acgatgcaac  540
agtggtctct ctaaacaaat aaatgaggca ctcgagaggc caatacgtaa gcgtttaccc  600
cgattagatg cattacgcta catacctatc tatgaagaag atgcttgcca taacaagtct  660
ttactaagac ttgcaaagtt gggattcaac cacctacaat ccttacataa gaaggagctt  720
agcctacttt ccaagtggtg gaaagctttt gatgttccaa ataatctaca tttcacgaga  780
aatcgattgg ttgaaaacta tttctgggta cttggtgtct actttgagcc tcaatattct  840
cgtgctagag ttttcatgac aaaagtgatt gcggttcca cgatttaga tgatacttat  900
gatgcatatg ctacttatga tgaacttgtt atctttacgg aagccgttca aaggtggtca  960
gttactatca tggatgaatt accagattac atgaaactga tatacaaaat cctcttagat  1020
gtttacgaag aaatggagga aacgatggca aaggaaggaa aaggccatca tgttaacttt  1080
gccaaagagc cgatgaaaga gatgattaaa aatttcatga tcgaagcaaa atggagaaat  1140
gaggggtata taccaacagt ggaagaacat aaatcggttt ctttcatgag ctgtggatac  1200
aaaatgctta caatagcaag ttttgttggc atgggtgaca taatcacaga tgagtccttt  1260
gaatgggttc tcggtaatcc tccacttatt aaaggttcaa gtgaaatttg caggcttatg  1320
gatgatatcg taggtcacaa ggaggagcaa aagagaaacc atgttgcatc tgtcgttgaa  1380
gcttacatga aacaaaatga tgttaatgag gagtttgtgt ataacgtatt caataaacaa  1440
gtcgaacaag catggaaagc tatgaatcaa gaatccctta aatgtaaaga tgtcgttcct  1500
ctacctctta taatgcgtgt gattaatctc gcacgtgtta tggataccct gtataaatat  1560
gatgatactt ttacgcgtgt tggagaagaa ctcattggtc acatcgaatc actatttgtt  1620
catgctatga gtctttag                                              1638

SEQ ID NO: 7                moltype = DNA   length = 339
FEATURE                     Location/Qualifiers
source                      1..339
                            mol_type = genomic DNA
                            organism = Stevia rebaudiana
SEQUENCE: 7
atggagatgg agaaaggaag aatttgtgta actggaggaa cagggtattt agcatcatgg  60
atcatcaaaa ggctgcttga agaagggtat tccgtaaata ctaccgttag atctcaatca  120
ggctcaaaga aagatgtgag ctacatcaca aacttacccc tagcttcaga gagactcgaa  180
atattcgatc agatttaag caaaccggag actttgaggc acccgatcaa aggttgcatt  240
ggtgtctttc atcttgcaca cccaatggat tttgaaggca acaataccgt agaagttata  300
actaaagaaa caattaagtg tagtttgggt attttataa                        339

SEQ ID NO: 8                moltype = DNA   length = 1281
FEATURE                     Location/Qualifiers
source                      1..1281
                            mol_type = genomic DNA
                            organism = Stevia rebaudiana
SEQUENCE: 8
atggaggttg aaaacgggtc aacattgatg atgaagaaga agagatgggg attccggtcg  60
aacccggagc tgaacatgtc gtcagataac accgtcagag gctttctcta tatgctcctc  120
tccaaactca acccatccga cacccgaccc gtcatccctc tcggtaacgg cgaccgtct  180
gctttcccat gcttccgtac ggcccaaatc gcagaagacg ccattgttga ttccattcgt  240
tctgcaaact tcaacggtta tggtcctact gtaggtattc ttcaagctag aagggctgtt  300
gcagagtacc tttctcatga tcttccatat aacttatcac cggatgatgt gttcttgaca  360
ctcggttgta cgcaagcgat tcaaaccata ataaccgttc ttactaatcc aaaagcaaac  420
atttactcc cgaaaccggg ttttccatat tatgaagcga ttgctaaatc atgccatttg  480
gaagttcgtc actttgacct tcttccagac aaagattggg aggttgacct tgactcggtc  540
aacgctcttg cagatgagaa tacggttgca attgttataa tcaaccctgg aaaccccttgt  600
ggaaatgttt tcacacacca acatctgcaa aaggttgctg aaacttcaaa gaagcttgga  660
atattagtga tttctgatga agtttatgat catcttgctt ttggaaaaaaa ccctttttgt  720
ccgatggcga aatttgcatc aattacacct gtgatcacac ttggttccat ttcaaaaagg  780
tggatcgtac ccggttggcg gtttggttgg cttgttatca acgatcataa tggcatcctt  840
aaagaacacg ggatcattga ttgcattaca gcatatctca gtatatcctc agacgctccg  900
acgtttgttc agggtgcagt tcctgatatc ctttcaaaaa ccaaagacga tttcttttt  960
aagatcgtaa gtataataaa agaagctgca aatatctgtt acgaggggat tcaagacatc  1020
cccggtataa tttgccccag taagcccgaa ggatccatgt ttgttatggt aaaactagat  1080
atgtcagtgt ttgaggatat taaggatgat gtggactttt gtgtgaagct tgctgaagag  1140
gaatcagtta taatccttcc aggtaaaagt gtaggattga caactggtt acgagtaaca  1200
tttgctattg agccttcagc acttaaagaa ggaatcaaga gacttaaagc ttttttgtgta  1260
aaacacacca agaaaccatg a                                          1281

SEQ ID NO: 9                moltype = DNA   length = 1443
FEATURE                     Location/Qualifiers
source                      1..1443
                            mol_type = genomic DNA
                            organism = Stevia rebaudiana
SEQUENCE: 9
atggaggaag gacttcaaac gccacttgtg ggtcaagaat caggaaagtg ggtcaggtct  60
tacagcaaag atgagatttt ttgtgagttt aagaaacaat tgtatttagc aggaccttta  120
atgacagtta atctgttaat ttgtgggtta tcgatgattt cggtgatgtt tgtgggtcat  180
ttgggcgagc ttgctttatc tggtgcttca atggctactc tttttgcttc tgtaactggt  240
accagtttaa tggttggaat gggtagtgct ttagacacat tttgtggaca atcttttggc  300
gccaaacaat atcatatgtt aggaatccat aaacaaagag ccatgattgt tctttttatca  360
accagcatcc cactcgcttt catttgggca aatgccggaa aattgctcgt ttttcttggc  420
```

-continued

```
caagatcctg aaatttcagc cgaagcgggc ctctatgcaa gattcatgat accaagtttg   480
tttgcaaacg ctttacttca atgtcacgtt cggtttcttc aatcgcaaaa caatgtgttt   540
ccaatgatgt taagcaccgg gtttacaacg ctacttcata tcttaatttg ttggattatg   600
gtgtttaaat ccggtttcgg gagtagaggt gcagctttgg ctaatgcgat atctctttgg   660
attaatgtgt tgttgttagc gatttatgtt cgcgtttcac cttcatgtaa aaaaacttgg   720
actggtttct caaaagaggc ttttcataat attccaacat ttttgaaact tgcagttcct   780
tctgcagtta tggtctgttt ggagatatgg tcgtttgaaa tgatggtgtt gctatctggt   840
gttcttccta atccacaact agaaacctca gttctttcta ttagcctgaa tacatgctca   900
atgatttaca tgattcctct tggtctaagt gctgccacaa gtgtaagggt ttcaaatgaa   960
ttaggagctg ggcgtgcacg cgctgcacgt ttagcaatac gcgtttcaat ggcttctgta  1020
gttacagaag gcattttggg tgcattaatc atgattttgg gccgaaaact atggggggtat  1080
tgttatagta acgaagaaga agttgtgagt tacattgcgc aaatgatgtt gcttcttgca  1140
ggatctcatg ttgttgatgg cattcaatct gtactttcag gggccgttag agggagtgga  1200
cgacaaaaaa taggcgcgat tgtgaactta ggtgcttatt atttgatcgg gattccttta  1260
gcgatcgtgt ttgctttgt gcttcatttg ggagggaagg gattatggtt cggtatcatt  1320
gcagcattgg tagctcaagc attatttctt ttcatattaa ctttgtgtac gaattgggaa  1380
aacgaagcaa aaaaggctaa tcaaagagtg tatgactcta tcacccgaga tgaagtatcg  1440
tag                                                                 1443
```

SEQ ID NO: 10          moltype = DNA   length = 939
FEATURE                Location/Qualifiers
source                 1..939
                       mol_type = genomic DNA
                       organism = Stevia rebaudiana SEQUENCE: 10
```
aagaagagat tattagtaat cggaggcagt ggttacctgg gtcagcatct gctacattcc   60
tttgcagaat ctcctctgga tctatcaatg gcgttcacac atcattcctc ttctcccctg  120
cttcctaatg ctactgcctt tcaagtcgac ttgcaaacgg gtcaaggttt tgactcaatc  180
tcccacaaat ttggccagcc tgatgtagtg gtaaattgtg ctgcactttc tgtgcctcgt  240
gcttgcgaga caaacccaac agttgccatg tcagttaatg ttccttgtac actcgtaaac  300
tggttatctg gtttttactca aaccaatacc aatactaata ctcttcttat tcatctcatca  360
actgatcaag tttatgaagg aacaaagtcc ttttataaag aagaggatga aacccttgct  420
gtaaacgtat acgaaactc aaaagtggca tcagaaaaat acattttgga aaactggtca  480
aactttgtga ttttaagaag cagcattatc ttcgggccac aaactgtttc acctgtctca  540
aaatcacttc ctattcagtg gatggatagt gttcttgcta aaggacaaga agcagagttt  600
ttccatgatg aatttcgctg cccggtttat gtcaaggatg ttgtaaatat catacaaatg  660
ttaacccaca gatggattc agatggcaag aaaagtcagt tgcttctaaa tatgggtgga  720
ccaagtaggg tatctcgtgc tcaaatggct gagacagtgg ctcgtgttag aggttacaac  780
acatcattga tcaaaccagt atcagcctca tcggttgatc gtggggtgaa gtcaccggct  840
gacatatcca tggatataag taagttgatt caaacactcg attttacacc tacttcattt  900
gaagatggtg tgaagttgac tattgagacc attaattaa                          939
```

SEQ ID NO: 11          moltype = DNA   length = 1191
FEATURE                Location/Qualifiers
source                 1..1191
                       mol_type = genomic DNA
                       organism = Stevia rebaudiana SEQUENCE: 11
```
atggcttcct ctgtaactgc actcgctcga cttgttcacc taactccttc tacaaaatca   60
aaccctaaac ccctcttcac tttcttcaca ctcaaatcat catattcccc aatcgtatca  120
tcatcatcat cattactatc aatgtcgtat gataaacaat cgctgctgc caagaaagct  180
gcatcccttg ctgctcgtct ctgccagaat gtccaaaaag gactgttgca atctgatgtc  240
cagtcaaaat ctgataaaag tccagtcaca gtggctgatt atgggtctca agttcttgtg  300
agctttgtac ttcaaaaaga acttcctgat caaacattct cactagttgc agaggaagac  360
tcgggagatc ttagaaaaga agaatctcaa gaaacccttg aacgtatcac gaaattagta  420
aatgatacga tcgctaatga tggaagttac aaagtgtctc ctttatctga tgcagatata  480
ctcactatca ttgatagtgg tatgtctgaa ggaggctcta ttggacaaca ctgggttttg  540
gatcctattg acggtaccaa aggtttttta aggggtgatc aatacgcgat agcgttaggt  600
ctgttagacg aagggaaagt ggtattaggt gtcctcgcgt gtccaaatct cccattggaa  660
tcaattacaa atcaaaatgt tgttactaag acagctgcag gttgtttgtt ttctgcacaa  720
ttgtcatgtg gaacattcat ggagtctcta gatggatcgc cacctgtcaa ggtgcatgtt  780
agcaacacgg agaatcccga agaagctgca ttctttgaat catatgaagc tgctcattct  840
tctcacagtt tatctggctc tatagcaaag aaattggggg ttaaagcacc accagttaga  900
atagacagcc aagcaaaata cggtgcattg tcacgaggag atggcgcgat atatttaagg  960
tttccaaata aaggatatcg cgagaagata tgggatcatg ctgcaggata cattgttgtt 1020
gcagaagccg ggggtgttgc ctcggatgct tctggaaagc cattagactt ttcaaaagga 1080
agatatctga atcggatac gggtattatc gttaccaacc agaaactgat gcccgcggtt 1140
ttaaaggcgg ttcaagattc actcaaagag gaagctttac catcactta a            1191
```

SEQ ID NO: 12          moltype = DNA   length = 1614
FEATURE                Location/Qualifiers
source                 1..1614
                       mol_type = genomic DNA
                       organism = Stevia rebaudiana SEQUENCE: 12
```
atgatggtat gcatagacag ttcacccgat tcacacgcaa ggttcctaac gaacgcaaac   60
aaaatgattt tgataaaaat ccatgatgtt ctaaaaatgg tatgtgacaa acaccggtta  120
cttcttgctc aaacatgggc tctgtcccaa cacacaagtt cgtatcccca tgaaaaagtc  180
attaaaaata gttgtggcag ttttgacatc agatgtgtcg ggaaagtctg catgtcaaga  240
```

-continued

```
tccggtctac cttttcatgt tcaagaaatg cgtatgtggc ctttctttaa agcatctaaa    300
gaacgacacc ttgacaagtc ccgtggactt gttggcaagg cgttgttaac ccacggttca    360
tgtttttgtg aagatgtcac caaactcagt gaagaagagt acccttttggt ccactacgca    420
cgcatgaaca ggttgaccgg ctgctttgca attttcttgc atagtattga agccaatgat    480
gactacgtgt tggagttttt tctaccgaca gacatcaaac acagttggca ggtatgccac    540
ttggtccaaa ctttgaagca aaatattcca acaggttcgg gatttgaact tggtgacagt    600
tccattatac acatcgttga accgtctaca gaagaagtag atatatcttt aagtatagac    660
ccttgtacaa tccaaatagc ctcgggtata acaacaaata acaaccaact tgaaatggct    720
acatcagatt cagagttaat ggttgtacat atggctaaaa ctgactccgc aagtgtatca    780
aacccatggc catataaaga aacttacgat gataaactca ctaatattat cactaacact    840
gaaaatgtga cgggagatga tatcagtgag tttatcatcg taagagaaaa tgaaaaaagc    900
atgagcaata aaattagtga tgccagaaa aaaagcaacg gttcaaaaaa aggcagaaag    960
cgtaaaaatag actctcttac aatggaggaa gttgtgaaac attttggaaa aacaatggat   1020
caagctgcta atagccttaa tgttggtcga tcgcacactg agcgtttttg ccgagaacat   1080
gatatgccaa gttggccatt gacaaagaac ataaacaaaa acatccataa taccgactta   1140
gagccatcag aaaaagcaca acaaaaacaa aacttgctac caaattttat atacgtgaca   1200
acattgctga tcgtgtggtt gagacggtgg agaaataaga tttcaaaaag gaatgcaaaa   1260
cccgtatata caatgaataa tatgaacaac gcgtattcac agatcgagtctt            1320
gttcatgcat tcccaaaaaa gaccgtagcg aggatctcag atataaagat ggtgacagtg   1380
aaggcaactt acaaagatga tatgattaag tttcaattcc ctacttcatc ggacctttg    1440
aaattaaaaa atgaggtggc acaaaggatt aagttagaaa agagaagggt ttgtttaaag   1500
tacaaggatg aagataatga catgatttcc cttgcttctg acgacgactt gaagtttctt   1560
ctagatctta cagctaataa cagtactatc agattactcg ttgattactt ttaa          1614
```

```
SEQ ID NO: 13          moltype = DNA  length = 654
FEATURE                Location/Qualifiers
source                 1..654
                       mol_type = genomic DNA
                       organism = Stevia rebaudiana
SEQUENCE: 13
atggctcaac ctaacgatgc acctgcattc cctccaattt cggtcatcgg tgatcagttc    60
gtttcactaa aaccacttca aattatagtc gaaaggtatc cttgtagata cattctgatc   120
accaacatta accatgaaat cttgctaaaa gtaaaaccat acgacaagac cttccatcac   180
cagcgtgtgc tacttgatcc taacgacaaa cccatagcgt tgctccgtga taagaatttg   240
agtatgcata gtagatggaa tgtatttagg ggtgaaagta aagacgattc ggacatgga    300
ctaagcgcaa aaaacgaaca catgatccag tttaagacca atgttagtgt gacgttggga    360
aagagcagca atgatgattg tgatttgagg attaaaggga gctggaagaa aggaaactgc    420
actatttata tcggagattc gtcaacagta gtggcacaga tgcaaaaacc ggaaactttg    480
aagcacgcga cggaaaaata catagtgaca attcagccta acatggacta tgcaggtgtg    540
gttgcacttc tcgcaattat tgatgccatg gaaaacccta aggaaaataa atctgtgggg    600
cttgaaactg cagcaggtgt ggttaatctt actagtgcag ttttgtcgat ttag          654
```

```
SEQ ID NO: 14          moltype = DNA  length = 2286
FEATURE                Location/Qualifiers
source                 1..2286
                       mol_type = genomic DNA
                       organism = Stevia rebaudiana
SEQUENCE: 14
tttctatgga ccagaatcgc acctaacatg gttgtgattc caaaattgtc gaaactgaaa    60
gttcatggtt tgaagaagtt gaagcaaata tgggctagta gtagtgaggc agataatgtt   120
tcaatgttga aggagattga aatatatgat tgtaatagtc ttgtgaatct ttttccaagc   180
aatccaatgc gattacttac tcatttggaa gatcttaaag ttttatggtg ttgctccatt   240
gaagtgttat tcaacataga cttgggtaaa attgagcaac atataagcta caacagcaac   300
ttaagaagga ttatagtgtt tgacctaaag gagctaaaag agctgtggag gatacatgat   360
gaaaataact atgatcacct tattgttggc tttcaagctg ttgaaactat ccgagggtgt   420
aagaagttta gaaatgtatt cacacctacg aaagccaatt ttgatatgag aggacttacg   480
gacatcgtga ttcagagtga taaagatgca gagattactg gtatatcaaa agaggatgat   540
gatacgtcta ctatagttgg attcccatca tatcacctca cacgcgcttt taatcaaatt   600
cataggattg gtttttattgg attagaaaaa gcagaagtgg tgtttggaat tgagaggcca   660
agtactaata cagaaattca acaaccacca ttacttccct gtcttgaatc tttatttttg   720
tggaaaatgg agaagatgag tcatgtgtgg aaatgcagca attggaatat tcttcacaaa   780
catcacccac aatcctcatt ccaaaacctc acagagatat acttggagga atgcaaacgc   840
attaagtact tgttttcacc tctcatgtcc aaacttcttt ccagcctaaa gagactcgaa   900
ataaaaaact gtgaaggtat tgaagaagtt gtttcaaata gagatgacga tgatgatgat   960
gatgatgaag cattgactac atctacgaca accttgttcc cgtgtcttga ttatctacaa   1020
cttaggtacc taagaaatct gaaacatatt agtggtggtg ttgttaaggg gaaaactaat   1080
gtggttcatg ataaatttaa gttttctcaa gcggatgtat ggtcttgtcc ttctttatca   1140
attctgattc catctgatgc agcactgcaa atgcaaaagc ttcaaaaagct gaccatatgg   1200
aattgcccat ccatggtgga ggtatttgaa agtaaaaata tcaacaataa tattgtttat   1260
agtagtaaca ctgaccaaac aagcgtctca ttggcaacac caacaactac tactatgcat   1320
catgaactaa ccaacctaag gatattgagc atctctaaat gtgacctatt ggaatatata   1380
ttcacatttt cgacacttga acgccttaag aaacttgaac agttgagcat ttatcattgc   1440
aaagctatga aagtgattgt gaaggaagaa cacaaagagg aattatcaaa ggtggtcatg   1500
cctcgtttaa aatcaattca actgtatgat ctaccaaatc ttgtaaggttt ctttgtaggg   1560
acgaatatcg actttgagtg gccatcatta gataatgcta tgatcaatga ttgcccccaa   1620
atgatggtgt tcatctcggt taagtcaacc gctccgaagc tcaagtttat acacacatcg   1680
ctaggcaaac ataatcttga atgtggcctt aactttcgtc agatgccacc cccaacttca   1740
aacagtatgt cagcttggtc ctttcataat ttggtcgaat tacatttgga atataaagat   1800
gaagttaaaa agattgttcc atacaatgag ttgctacaac tgcatgttct tgaaaagata   1860
```

-continued

```
agtgtagagg tgtgtgagag tgtagaggaa gtatttgaag tcacaaacaa tgagtcacaa   1920
actgttgtga aaattccaaa gctaagagaa atgaatttag aatatctaga caatctcaag   1980
tatatatgga agagcaatca gtggagtaaa ttggagtttc caaacctaac aagattgtct   2040
attgtcagat gtgacagttt agaacatgtt ctaacagctt ccatggttgg tagtctcatg   2100
caactccaag agctacatat aggtgagtgc gaaaatctta aggtaatcgt gaagaaaaaa   2160
gaagaagaat gtgatggcaa agtaggtgag attaagtttc cttacttgaa gttcttaaaa   2220
cttgatactc tttcaagtct caacggattt tgcttagagg aggaagatat ttcatttcca   2280
tcaatg                                                              2286

SEQ ID NO: 15            moltype = DNA   length = 2883
FEATURE                  Location/Qualifiers
source                   1..2883
                         mol_type = genomic DNA
                         organism = Stevia rebaudiana
SEQUENCE: 15
atggattcaa agcaaccatt aatctcgtta ttttcttctt ctcctgttca tttcctcttt   60
tatgctcttg tcataattct aaattccacc accatcgcag ctggaaatga gaccgatcat   120
gaggctttga tacatatcaa gttgatgatc actcatgatc catatggata tctaacctca   180
tggaaccatt caattcattt ctgtgattgg agtggtgtta tatgtgggaa gcgacataga   240
agagtgactt atttagattt agactcacaa ggtctacaag gctctttgtc tcctcacgtc   300
ggaaacctca gtttccttcg tggaatttat ctctataaca acagctttga aggatgcatt   360
cctcatgaag tcggtcgcct tttcaggcta cgtatcctit acttgtatca aaacaaattc   420
gacacggtta ttccagctaa catatccggt tgttctagcc ttgaaattct tgatctttcc   480
accaacgagc tagttggaag catacccaag gagatcagtt tcctctccaa actcacttat   540
ctttcactcg atgataataa gttatctggt ggaatcccac ctttcttggg gaatattaca   600
caaatggaaa agttcggtgt tgtccgaaat ccgatggggt ggattacc catattagag   660
ggtcgttggg agttttaga agaaatttat tgtgggggtt gtaatctatc tggaaccatc   720
cctcgttcga tttataacct ttcgctacta acatatttta gctttcctga taacaaactc   780
accgatactc ttccagcggc catgggtgaa ttgctccctc aacttgttgt ggttgagtta   840
tggaataacc aactaactgg accgcttcca ccgtctcttt ctaactgttc gagattagag   900
aaacttgaaa cgagtgtgaa caagtttagt gggaagttga gaatcgactt tgcacaatta   960
agagatattg agattatatc cttaagtacc aataccttitg gaagcaatga agttgatgag   1020
atgaagttca ttgattcttt aataaactgc accaaattaa aatggttgga tcttggtact   1080
tgtaagtttc aaggagtgct ccctcgatca ataggtaatc tttcaaatca acttcatcgt   1140
ctatatttag atgaaaatca tatacatgga aacctcccta tatcaatagg taatctagtt   1200
ggtttagaaa tgttatcact agaagaaaac caattcacag gaaacatccc ctcaaccgtt   1260
ggtaaccttc gaaagctaca agctatttat ttatataaaa atcaacttic aggagaaatt   1320
cctaaagcca taggaaactt aacatcattg aacacacttg atttatcttc aaatatgttg   1380
gtaggggtga ttccttcaag cttggggaat tgtcatagtc ttttagagtt gtaccttggt   1440
ggcaataaac ttcacgggaa aatccctaaa caacttttc aactctcatc tctatcgaaa   1500
acattagatc tctctcaaaa caacctgtat ggttcgtttc caactgaggt cggaaatctc   1560
aagatgttgg gtaatttgga tatatcttat aatagtttat caggtagcat tcctagtagc   1620
attgatggt gtgctagcct ttcaagattg tccctcaaag gaaacttatt tcaaggtaag   1680
ataccaccat cgttaaattc cttgaaagga ttgttggaac tcgatgtttc tcataatcat   1740
ttatcaggtc aaattcctcg attcttggaa cgactagatt ttttgaacct ttcatataat   1800
gattttgagg gtgaagttcc aatcctagga gtgtttacca atctaagtgc attctctatt   1860
ttaggaaaca gtaggctttg tggtggtttg gttgaacttc atttacccaa atgcaaggat   1920
acaaagaaac atacaaaaaa atttcacctc tttgtaatag tcattttggt tgcattcaca   1980
ctttgcttca ttttatgttt agcatatgct tggcataaga agaaaagaaa gagtcattct   2040
tccgaatcat caatgagcaa acgtttcatg aaagtttcat atagtcaact tcttaaggct   2100
accgatggat tctctgaaac caatttgatt ggaaatggtg ggtttagctc cgttttataaa   2160
gggatacttg atgaagaaga tggaagattt gttgcaatca aagttctaca tcttcaaaat   2220
agaggagctc aaagaagttt tatgagggaa tgtgaagtat ggcggagcat tcgacaccga   2280
aacttgttaa agataataac ttcatgttca agtattgact tccaaggaaa tgatttcaaa   2340
gctttggtgt acgagttcat gcctaatgga agtttacatg attggttgca tccaacttcg   2400
agattaaacc ttcttcaaat aataaatatt cttatggatg tcgcaaatgc acttgattat   2460
attcacaatc gatgcgtgcc aagcattgtt cacggtgact tgaagcctag caatattctg   2520
ctcgatcatg atatggtagc tcatgttggt gactttggtt tagctcgatt tattgaaacg   2580
acgtcatacc aaaacagctc aaccgggatt agaggaacaa ttggttattc ccctccagag   2640
tatggtcttg ggggtgagat gacaagtagt ggagacatct acagctttgg aatattacta   2700
ttagaggtga tgaccggtaa gaatccaacc gatgacatct ttaatgaagg tcttagcctt   2760
cataaatttg cttccatggc cttgctagac cacgtaaccg acattattga tgtgaacatt   2820
ctgaaccttt ttcaaaacga tgaaaatatc atacaaaata atgaagtaga tgcaatggaa   2880
taa                                                                 2883

SEQ ID NO: 16            moltype = DNA   length = 2247
FEATURE                  Location/Qualifiers
source                   1..2247
                         mol_type = genomic DNA
                         organism = Stevia rebaudiana
SEQUENCE: 16
atgcatttaa acatacttct agcaatagca gctattgcag ctttcatggc ggcaattaat   60
cctcaaaact ccctaaattg tgaaagttca tgtggcaacg tgactatcac atacccattt   120
ggttcaggtc caggatgcta ctacagtcca gatttcttgg ttacttgtaa ccgatcaacc   180
gatgtacccg taccatatta cggactaagt acaagcaata ttgttattc aaatatgtcg   240
acaaacaaga gtgaggtgga gatcatgatg tttgtagccc atgattgcta caatacttct   300
ggcccgactg gacgtaacag tccatatttg cggtcgagta atttccggat ctcgtccaag   360
aacaaattcg tcgccatcgg gtgtgatacg gaagcagatt ttttaggaag tagagggaat   420
tattctgata ttagtagcat atgctcttct agatgtgata taaatagcga tattactaac   480
```

```
ggatcatgtt caggaattgg gtgttgcgaa ttagacgttc cagaaggaat ggattatgtt   540
caaatgtcgg taagtagctt taataaccat acgaatataa ccgactttaa cccttgtggc   600
tatgggttct ttgttgaaga aggaaagttt agcttttcta ccacgaacct gcttgatttt   660
gaaacaaaga tgccgatgtt acttgattgg gcaattggaa acttgacttg tgaagaagca   720
aagaacacag ataatgagtt cttatgtacg ggaaatagta catgtgatca agattataaa   780
ggtgttggat atcgttgcgt ttgcaaagaa ggttatagag gcaatccgta tgatccaagta  840
aatggctgca aaaatattaa cgagtgtata gaacgaactc atacatgcca tgatgatgct   900
tggtgtcatg atacggatgg aaaactacacg tgtgaatgtc gaaaaggtta ctctggagat   960
ggtacgaaga ttggaacagg ttgcactgct aatcaatcct cctcaataaa gatagttgta  1020
ggtatctcag cttctgctat atttcttctt atatttgtca cgtggttgta cttgatacta  1080
aagaagcgaa aggagatgat gctgagagag aagtcttta aacaaaatgg cgggataatg    1140
ttggagcaaa aatatttgtc tggagaaggg agttctcata atcaagcaaa agtcttcact  1200
ttagaggagc taaaggggc gaccaacaac tacgatgaga gcaggattat tggtaaaggt  1260
ggacatggca ccgtttataa aggagttctt tctgataaca gaatagttgc cataaaaaag  1320
tctaaaatac cagatcaaaa tgaaaacgag attgaacaat ttatcaatga agttgttatc  1380
ctgtcccaga taaatcatag gaatgtagtg aagttgattg ggtgttgttt ggaaacagaa  1440
ttcccattgt tggtttatga gttcattcca aatggcacac tttctgatca catccacacc  1500
aaaggcaagc tgtcacctat tacatggaac atccgactta gaatagcaac ggagacagct  1560
gaagcacttt catacttgca ttctgctgca tcagttccaa tcatacatcg tgatgtgaag  1620
ccatcgaata tactttggga tgacaactat gtagcaaaag tggccgattt tggagcatct  1680
aagctaattc ctattgatca gatcgagttg gctactattg tgcaaggaac actaggctac  1740
ttagatcccg aatatatgca aacaaatcaa cttacagata aaagcgatgt ttatagtttt  1800
ggggtcgtac tggcggaact tttaacggga aaaacagctc ttagctttga taggccagag  1860
aaagagagga atctagctat ttattttcta tattccttaa aagaagggag actcttccaa  1920
attcttgatg aacaattaca actaaatgat gttcctagcg acatcattca agtttcaaga  1980
ctggcagaaa gatgcttacg tgttaaaggt gacgaaaggc caaccatgaa agaagtagcg  2040
attgagctcc aaggaatact ggcatcaatg atacaaaagc atccatgggt acaaaatatt  2100
acaaatgaag aagaagatga gtatttgctc aaagaattaa acaatgacta tgattctaca  2160
aatgttggca atgtaagcgt tgtcaactca agcacctttg atagcatgag caatcattct  2220
attttacccca ttgctagtgg tagatga                                     2247
```

SEQ ID NO: 17          moltype = DNA   length = 498
FEATURE                Location/Qualifiers
source                 1..498
                       mol_type = genomic DNA
                       organism = Stevia rebaudiana
SEQUENCE: 17

```
atggcgacca cggtttacgc ggcggcaact tcaacctcta tggcggctac cgccggtatg    60
ctgccacgtc ttccgacgag aatcaccacc gctggtttct ccgccgtacc taccctcccg   120
gctcgttcgt tttctacctc cgtcaaacag gtttcagggt caaaaaggtc aaatcttttc   180
cagataaagg tctcagaaga cgcatcatcc gcccccgatg caaatgagtt gttcaatgac   240
ctaaaagaaa agtgggatgc agttgagaac aagtcaactg tcataatcta tggtggagga   300
ggaattgttg caatttggtt atcctcaatt gttattgatg caattaattc tgtgccgtta   360
cttccaaaga tcatggagtt ggtcggactt ggatataccg gatggtttgt ctaccgatat   420
ttgctcttca gtcgagcag aaaaagagcta gcgacagaca ttgagtccat aaagaagaag   480
attgcgggga ccgaataa                                                 498
```

SEQ ID NO: 18          moltype = DNA   length = 1308
FEATURE                Location/Qualifiers
source                 1..1308
                       mol_type = genomic DNA
                       organism = Stevia rebaudiana
SEQUENCE: 18

```
atggaaaaga gggatttgga gcttggagac atacgcattt tacaagacgc cgtccaaatt    60
cttgttgatg gggtgaaaag agggcataat cgtacaaatc aatcttcacc gttgatttcc   120
aaagactata cttgttcaga aatgcaggaa gtctttattg gacttgcgca cagttgctac   180
cttttaggta gacacagttt aggtgcagag ctgaaagaaa gttatttgat taatctaatg   240
agtcgcatcc cttccccaga agaggaaacg ttaaaatcat gtgcgcataa ggtctacacg   300
tcactcaaac aaatcaagtc atgttatcct gttcatataa ttaaggatca agagcacgag   360
ttaggtgatg ctgaaattgt caatgttatt gttacagatg cttgtttcat acttgaattc   420
gtcaacacga tttcgaaata tgataaatca tttcgcgggt acatgatcct gacccaaaat   480
ataatttctg acttggtgtt ggtacaaaac caaatccctt tctttattct tgatgaaata   540
ttccggtgca ctatattaaa attcaagcca aacatctccc ttgttgaatt tctccttcca   600
cttctaaatc tcctcaaatat tttaaatcc gatataaaat tccgacaatat ttccgttagt   660
accactagtc atatacttgg ccttctacac gaatgctaca agcctcatta tcccgttgca   720
tcaactttcg taacatcaac aatccaatcg actaaagatc tagataggc agggatcaac   780
atagaacaca accgaaatcc aaaatggttg ttggggatgg atgtgaagtt acataggttc   840
ccgtgttttt catggtgtca gggtaagcct actttcagaa tgccagcatt atatgttcat   900
gaattcacta agttggtttt aatgaacctt attaaatacg agcatcactt tgatcaagat   960
cacaagtatg ttacatcata tgcttatacc atagatatgc tagtgaatac tgaagaagat  1020
gttgctacgt tggtagagtc aggagtcctt gtcaacaata tgggttcaaa taaagaagct  1080
actaatatga tcaactccat atgtaataaa gtcacactgg aacatttctt ttacggtgaa  1140
gagtggcaaa aattgaataa ttactgcaat agttactggc aaaaaaatat agcacggttg  1200
aagaggactt acttcagtag tccatggact atcattgctc tgttcgctgg aatcatccta  1260
tttgctttaa cagtggttca gaccgtttat accattgaaa gtgcctga                1308
```

SEQ ID NO: 19          moltype = DNA   length = 813
FEATURE                Location/Qualifiers
source                 1..813

```
                        mol_type = genomic DNA
                        organism = Stevia rebaudiana
SEQUENCE: 19
atggaggcgc tctattccaa gctgtatgat aagtacacta agctcaaggc aaaaaagact  60
tctgaaacag agcgactaag tctggatcaa gaagaaaat tcaaaactta tgtgtctgct  120
gcagatgaac taattggcta tttaacaagc gaaaaggaca agttatctgc acagattagt  180
gatttgagac acgaaattgc ctcaatcaga tctaccaagg acgaagagga acaaatgcat  240
gaaatgatgt tgatggaaga aaagcagaaa aacaaacaac tttcagaaga aatagagagg  300
ctgcagagaa acaaatctga ttccagcgat aaacaatctt caggttctcc actttcattc  360
cacaattcaa caaagagaaa acgactcatg ctgcatgaaa aagaagttgt tgatgaagat  420
aacatcttct ctggagtttt tactaatgat gataatacac agcctaaatg ctgtcgtcga  480
aggcttagtg gtacagtaaa tgctgcctct gattcttcta gcaattgctg tatgtttcaa  540
gagcttgttg agtgcttaat cgacctcaag ttttcagttg gaaccccaat tgatgataat  600
atacaaataa ccgcggttca cgaatcaagt ggatactcat ttactttggg atgggtgagt  660
aagggagagg acgcgatgat gatgtaccgc gtgtcatcat tgggaacata tgagcgagtt  720
gcaccagaat ggatgcgcga tttgatgtta tttagtaaga gcatgttaag tgtctttttt  780
aaaagacttt cggtcctttt taaatcttca tga                              813

SEQ ID NO: 20         moltype = DNA   length = 507
FEATURE               Location/Qualifiers
source                1..507
                      mol_type = genomic DNA
                      organism = Stevia rebaudiana
SEQUENCE: 20
atgcctccgc cacatcccgc cggcccacca cccttcacgc cgccgtcatc ctccgctctc  60
tacaaacaaa attcatggtc accggacctt caccgggacg aggaatggat ccgccggaaa  120
gggaaaaatc tccaccgacg tcgccggaaa agcaaaagcg tcaccgatga agacatcgat  180
gaactcaaag cttgtttcga tcttggattc gggttcgatc attcttcacc ggaagtggac  240
gaccggcttt caactacttt tccggcgttg ggcttctatt acgccgtcaa caagcagtat  300
ctcgatacag tctccaaatc ttcatccatg tcgccatcgt cttcctcgtc gatttcatct  360
gcatctgctc tttcggaacc cgatttatct tctccatcaa gcagctctca caacataatc  420
aatcatgggg ataatccaca gacggtgaag actagattga gacaatgggc gcaagttgtt  480
gcttgttcgg tgagactacc atcatga                                     507
```

HIGH REBAUDIOSIDE M STEVIA PLANT CULTIVARS AND METHODS OF PRODUCING THE SAME

CROSS REFERENCE TO RELATED APPLICATION

This application is a divisional application which claims the benefit of priority to U.S. application Ser. No. 17/701,154, now U.S. Pat. No. 11,844,323 issue date of Dec. 19, 2023 which is a divisional of U.S. application Ser. No. 16/491,470, now U.S. Pat. No. 11,284,577 issued Mar. 29, 2022 which is a 371 National Stage entry of and claims the benefit of priority to PCT Application No. PCT/US2018/021389 filed on Mar. 7, 2018, which claims the benefit of priority to U.S. Provisional Application No. 62/468,937, filed on Mar. 8, 2017, the entire contents of which are incorporated herein by reference for all purposes.

SUBMISSION OF SEQUENCE LISTING

The Sequence Listing associated with this application is filed in electronic format via PatentCenter under the xml file PURC08USG1 Sequence Listing and is hereby incorporated by reference into the specification in its entirety.

BACKGROUND

*Stevia* is an important and valuable field crop for the production of sweeteners, sugar substitutes, and other consumable ingredients. Thus, a continuing goal of *stevia* plant breeders is to develop stable, high yielding *stevia* cultivars of *stevia* species that are agronomically sound. The reasons for this goal are to maximize the amount and quality of the sweeteners, sugar substitutes, and other consumable ingredients. To accomplish this goal, the *stevia* breeder must select and develop plants that have the traits that result in superior cultivars. All references cited herein are incorporated by reference in their entirety.

The development of new *stevia* cultivars requires the evaluation and selection of parents and the crossing of these parents. The lack of predictable success of a given cross requires that a breeder, in any given year, make several crosses with the same or different breeding objectives.

The foregoing examples of the related art and limitations related therewith are intended to be illustrative and not exclusive. Other limitations of the related art will become apparent to those of skill in the art upon a reading of the specification.

SUMMARY

The following embodiments and aspects thereof are described and illustrated in conjunction with products and methods, which are meant to be exemplary and illustrative, not limiting in scope. In various embodiments, one or more of the above-described problems have been reduced or eliminated, while other embodiments are directed to other improvements.

It is believed that the conversion of rebaudioside A to rebaudioside M in the plant requires minimal steps to accomplish. However, known *Stevia* species contain very little rebaudioside M compared to rebaudioside A, suggesting, that the conversion pathway is subject to negative effect of certain regulating elements in these plants. By identifying these negative regulators and disrupting their functionality, it is believed that the conversion pathway from rebaudioside A to rebaudioside M can occur more readily, resulting in a higher yield of rebaudioside M in the *Stevia* leaf An embodiment of the present disclosure is directed to producing *Stevia rebaudiana* plant cultivars which produce high levels of rebaudioside M as compared to native or commercially known *Stevia* plants such as *Stevia rebaudiana* Bertoni and *Stevia rebaudiana* Morita.

Another embodiment discloses the disruption of negative regulators of rebaudioside M biosynthesis. By disrupting the function of these negative regulators in *Stevia, Stevia* plants can be produced that are able to produce higher levels of rebaudioside M as compared to different *Stevia* varieties.

Another embodiment discloses a *Stevia rebaudiana* plant comprising at least one disrupted negative regulator gene in the rebaudioside A to rebaudioside M conversion pathway.

Another embodiment discloses a method of increasing the rebaudioside M content in a *Stevia rebaudiana* plant by inducing a disruption in at least one negative regulator gene function in the plant, wherein said negative regulator gene is selected from the group consisting of genes affecting metabolism, signal transduction and gene regulation, and other novel uncategorized genes.

Another embodiment discloses metabolism genes, wherein said genes are comprised of genes affecting sugar metabolism, mono-oxygenase content, terpene metabolism, aminotransferase metabolism, multi-antimicrobial extrusion protein metabolism, and methionine metabolism.

Another embodiment discloses metabolism genes, wherein said genes are selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10.

Another embodiment discloses a plant, or a plant part thereof, of the *Stevia rebaudiana* plant of the present application, consisting of leaves, pollen, embryos, cotyledons, hypocotyl, meristematic cells, ovules, seeds, cells, roots, root tips, pistils, anthers, flowers, and stems.

Another embodiment discloses signal transduction and gene regulation, wherein said genes are comprised of abiotic stress genes and biotic stress genes.

Another embodiment discloses signal transduction and gene regulation genes, wherein said genes are selected from the group consisting of SEQ ID NO:11, SEQ ID NO:12, SEQ ID NO:13, SEQ ID NO:14, SEQ ID NO:15, and SEQ ID NO:16.

Another embodiment discloses novel uncategorized genes, wherein said genes are selected from the group consisting of SEQ ID NO:17, SEQ ID NO:18, SEQ ID NO:19, and SEQ ID NO:20.

Another embodiment discloses a method for producing a high Rebaudioside M *stevia* plant comprising: (a) screening a population of *stevia* plants for a mutation in at least one of the following sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:17, SEQ ID NO:18, SEQ ID NO:19, and SEQ ID NO:20; (b) selecting a first *stevia* plant having said at least one mutation; (c) crossing the first selected *stevia* plant having at least one mutation with a second *stevia* plant; (d) screening the *stevia* offspring for plants having high Rebaudioside M; and (e) selecting a *stevia* plant having high Rebaudioside M.

BRIEF DESCRIPTION OF THE SEQUENCE LISTINGS

SEQ ID NO: 1 discloses the endo-1,3; 1,4-beta-D-Glucanase gene (STKS #1).

SEQ ID NO: 2 discloses the glucose-6-phosphate dehydrogenase gene (STKS #2).

SEQ ID NO: 3 discloses the cytochrome P450 716B1-like gene (STKS #3).

SEQ ID NO: 4 discloses the putative flavonoid 3'-hydroxylase cytochrome P450 gene (STKS #4).

SEQ ID NO: 5 discloses the KAH-like cytochrome P450 gene (STKS #5).

SEQ ID NO: 6 discloses the Isoprenoid Biosynthesis Cl Superfamily gene (STKS #6).

SEQ ID NO: 7 discloses the vestitone reductase-like gene (STKS #7).

SEQ ID NO: 8 discloses the aminotransferase gene (STKS #8).

SEQ ID NO: 9 discloses the MATE efflux family protein gene (STKS #9).

SEQ ID NO: 10 discloses the methionine adenosyltransferase 2 subunit beta-like gene (STKS #10).

SEQ ID NO: 11 discloses the SAL1 phosphatase-like isoform gene (STKS #11).

SEQ ID NO: 12 discloses the nitrate-dependent transcription regulator gene (STKS #12).

SEQ ID NO: 13 discloses the LURP1-like domain-containing protein gene (STKS #13).

SEQ ID NO: 14 discloses the RGC2 Resistance Protein gene (STKS #14).

SEQ ID NO: 15 discloses the LRR Receptor Kinase gene (STKS #15).

SEQ ID NO: 16 discloses the Wall Associated Receptor Kinase gene (STKS #16).

SEQ ID NO: 17 discloses a DNA sequence of unknown function (2672) (STKS #17).

SEQ ID NO: 18 discloses a DNA sequence of unknown function (5237) (STKS #18).

SEQ ID NO: 19 discloses a DNA sequence of unknown function (10666) (STKS #19).

SEQ ID NO: 20 discloses a DNA sequence of unknown function (13209) (STKS #20).

BRIEF DESCRIPTION OF THE FIGURES

The accompanying FIGURES, which are incorporated herein and form a part of the specification, illustrate some, but not the only or exclusive, example embodiments and/or features. It is intended that the embodiments and FIGURES disclosed herein are to be considered illustrative rather than limiting.

The FIGURE shows the expression pattern of cytochrome P450 716B1-like gene (STKS #3) among different *stevia* plant types.

DEFINITIONS

In the description and tables, which follow, a number of terms are used. In order to provide a clear and consistent understanding of the specification and claims, including the scope to be given such terms, the following definitions are provided. All rebaudioside contents are represented as a percentage of the dry weight of leaves.

High rebaudioside A: As used herein, plants described as having high rebaudioside A have a rebaudioside A content of greater than or equal to 9%, a rebaudioside D content of less than or equal to 0.3%, and a rebaudioside M content of less than or equal to 0.2%.

High rebaudioside D: As used herein, plants described as having high rebaudioside D have a rebaudioside D content of greater than or equal to 0.6% and a rebaudioside D/total steviol glycoside greater than or equal to 8%.

High rebaudioside D and high rebaudioside M: As used herein, plants described as having rebaudioside D and high rebaudioside M content have a rebaudioside D content of greater than or equal to 0.6% and a rebaudioside D/total steviol glycoside greater than or equal to 8%, and a rebaudioside M content that is greater than or equal to 0.5%.

High rebaudioside M: As used herein, plants described as having high rebaudioside M have a rebaudioside M content that is greater than or equal to 0.5%.

High stevioside: As used herein, plants described as having high stevioside have a stevioside content of greater than or equal to 7%, a rebaudioside D content of less than or equal to 0.3%, and a rebaudioside M content of less than or equal to 0.2%.

High stevioside and high rebaudioside A: As used herein, plants described as having high stevioside and high rebaudioside A have a rebaudioside D/total steviol glycoside less than or equal to 7.60% and a rebaudioside M/total steviol glycoside less than or equal to 1.9%.

Marker: As used herein, a "marker" is an indicator for the presence of at least one polymorphism, thus a marker can be the nucleotide sequence itself, or a probe, for example.

Plant: As used herein, the term "plant" includes reference to an immature or mature whole plant, including a plant that has been processed for steviol glycosides. Seed or plant part that will produce the plant is also considered to be the plant.

Plant Part: As used herein, the term "plant part" includes leaves, stems, roots, seed, embryo, pollen, ovules, flowers, root tips, anthers, tissue, cells and the like.

Rebaudioside A (RebA): As used herein "Rebaudioside A" or "RebA" is a steviol glycoside that contains only glucose as its monosaccharide moieties. It contains four glucose molecules in total with the central glucose of the triplet connected to the main steviol structure at its hydroxyl group, and the remaining glucose at its carboxyl group forming an ester bond.

Rebaudioside D (RebD): As used herein, "Rebaudioside D" or "RebD" is an ent-kaurane diterpene glycoside isolated from *Stevia rebaudiana*.

Rebaudioside M (RebM): As used herein, "Rebaudioside M" or "RebM" is an ent-kaurane diterpene glycoside isolated from *Stevia rebaudiana*.

SNP: As used herein, the term "SNP" shall refer to a single nucleotide polymorphism.

Stevioside content: As used herein, stevioside is the percent glycoside derived from the *stevia* plant.

DETAILED DESCRIPTION OF THE INVENTION

*Stevia rebaudiana* (Bertoni) is a herbaceous perennial plant of family Asteraceae, which consists of approximately 230 species of herbaceous, shrub and sub-shrub plants. *Stevia rebaudiana* is known to yield diterpenoid steviol glycosides (SGs), which are about 300 times sweeter than sucrose. Twenty-one diterpene glycosides have been identified in leaf tissues of *stevia* (US2011/0183056). Among these, four major steviol glycosides synthesized in the leaves of *stevia* are stevioside (STEV), RebA, rebaudioside C (RebC) and rebaudioside F (RebF). STEV account for 5-10% of the dry weight of the leaves while RebA accounts for 2-4% (Pande and Priyanka 2013).

Embodiments described herein relates generally to *stevia* varieties, wherein at least one negative regulator gene in the rebaudioside A to rebaudioside M conversion pathway has been disrupted.

Shown in Table 1 below is a listing of gene candidates that are believed to be involved in the negative regulation of the rebaudioside A to rebaudioside M conversion pathway. It is believed that the disruption of one or more of these negative regulation genes in *Stevia* will result in an increase in the conversion of rebaudioside A to rebaudioside M in the *Stevia* plant. All of the gene candidates are native to the *Stevia* plant.

TABLE 1

Negative Regulator Candidate Genes for Rebaudioside M Overproduction

| Category | Functional-Category | Candidate Gene (putative homologs) | Gene ID # |
|---|---|---|---|
| Metabolism | Sugar Metabolism | endo-1,3;1,4-beta-D-Glucanase | STKS#1 |
| | | Glucose-6-phosphate dehydrogenase | STKS#2 |
| | Mono-oxygenase | Cytochrome P450 716B1-like | STKS#3 |
| | | Putative flavonoid 3'-hydroxylase cytochrome P450 | STKS#4 |
| | | KAH-like cytochrome P450 | STKS#5 |
| | Terpene Metabolism | Isoprenoid Biosynthesis C1 Superfamily | STKS#6 |
| | | Vestitone reductase-like | STKS#7 |
| | Others | Aminotransferase | STKS#8 |
| | | MATE efflux family protein | STKS#9 |
| | | Methionine adenosyltransferase 2 subunit beta-like | STKS#10 |
| Signal Transduction and Gene Regulation | Abiotic Stress | SAL1 phosphatase-like isoform | STKS#11 |
| | | Nitrate-dependent transcription regulator | STKS#12 |
| | Biotic Stress Responsive | LURP1-like domain-containing protein | STKS#13 |
| | | RGC2 Resistance Protein | STKS#14 |
| | | LRR Receptor Kinase | STKS#15 |
| | | Wall Associated Receptor Kinase | STKS#16 |
| Novel Genes | With Conserved Domains | DNA sequence of unknown function (2672) | STKS#17 |
| | | DNA sequence of unknown function (5237) | STKS#18 |
| | | DNA sequence of unknown function (10666) | STKS#19 |
| | Without Conserved Domains | DNA sequence of unknown function (13209) | STKS#20 |

All *Stevia rebaudiana* planted across the whole world are 97-99% genetically identical with estimation of a 2 GB genome. Genetic differences comprise only 2-3% of this 2 GB genome among different *Stevia rebaudiana* plants and are the key attributes for *stevia* adaptability, growth performance, leaves sizes, disease resistance, variation in steviol glycosides composition and so on.

Deep short-read sequencing approach has been employed to quantify gene expression levels in samples with different rebaudioside M accumulations. To identify the potential negative regulators of rebaudioside M biosynthesis, candidate genes are selected according to lower expression levels in high rebaudioside M *Stevia* plants comparing to that in high rebaudioside A or rebaudioside D *Stevia* plants. Preference are given to selecting candidate genes with single-copy protein-coding sequences. The expression patterns of the selected candidate genes are validated across independent short-read sequencing datasets.

Embodiments described herein also provide for methods of disrupting at least one negative regulator gene in the rebaudioside A to rebaudioside M conversion pathway. Such methods may include, but are not limited to, ethyl methane-sulfonate (EMS) mutagenesis, site-directed mutagenesis, direct gene targeting (knockout), RNA interference, and CRISPR (gene editing).

Embodiments described herein also provide for methods of introducing a mutation into one or more negative regulator genes in the rebaudioside A to rebaudioside M conversion pathway, said method comprising applying a mutagen, wherein said mutagen is selected from the group comprising ionizing radiation, chemical mutagens, targeting induced local lesions in genomes, zinc finger nuclease mediated mutagenesis, and meganucleases, and selecting for a plant having a mutation in one or more negative regulator genes in the rebaudioside A to rebaudioside M conversion pathway.

Another embodiment provided herein discloses a *stevia* plant produced by the method above, wherein the Rebaudioside M content of the leaves is at least 0.5% of dry weight.

Embodiments described herein also provide methods for screening for *stevia* plants containing a disruption in at least one negative regulator of Rebaudioside M. These methods may include, but are not limited to, gene sequencing, SNP analysis, RNA-sequencing, and gene expression analysis.

Embodiments described herein also provide methods for introgressing the high Rebaudioside M phenotype into other *stevia* varieties in a plant breeding program by selecting for *stevia* plants having a disruption in at least one negative regulator gene, and applying plant breeding techniques such as recurrent selection, backcrossing, pedigree breeding, marker enhanced selection, or haploid/double haploid production, to produce novel *stevia* cultivars having high Rebaudioside M.

Another embodiment discloses a *stevia* plant, wherein the leaves of said *stevia* plant have a Rebaudioside M content of between about 0.1% and 2.0%, or between about 0.5% and 1.54%, for example, about 1.15% of dry weight. Higher Rebaudioside M contents, such as 3.0%, 4.0% or 5.0%, are contemplated by this invention.

Another embodiment discloses a method for producing a high Rebaudioside M *stevia* plant comprising: (a) screening a population of *stevia* plants for a mutation in at least one of the following sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:17, SEQ ID NO:18, SEQ ID NO:19, and SEQ ID NO:20; (b) selecting a first *stevia* plant having said at least one mutation; (c) crossing the first selected *stevia* plant having at least one mutation with a second *stevia* plant; (d) screening the *stevia* offspring for plants having high Rebaudioside M; and (e) selecting a *stevia* plant having high Rebaudioside M.

Another embodiment provided herein discloses a *stevia* plant produced by the breeding method above, wherein the Rebaudioside M content of the leaves is at least 0.5% of dry weight.

EXAMPLES

The following examples are provided to illustrate further the various applications and are not intended to limit the invention beyond the limitations set forth in the appended claims.

In order to identify the top negative regulators of Rebaudioside M accumulation, transcriptomic analysis was carried out using PACBIO® ISO-SEQ® and ILLUMINA® HISEQ® sequencing approaches. PACBIO® ISO-SEQ sequencing was conducted to determine the full-length genes models and post-transcriptional modifications, to assist in genome annotation and gene prediction. ILLUMINA® HISEQ® sequencing is to quantify expression levels of each transcript in specific tissues under different conditions. The selection criteria for the top negative regulators are: 1) protein coding sequences with lower expression in high Rebaudioside M *Stevia* lines; 2) consistent lower expression in high Rebaudioside M *Stevia* lines under different conditions (healthy and stressed); 3) show negative correlation with Rebaudioside M trait in expression networks. As an example, the expression pattern of a candidate gene, cytochrome P450 716B1-like protein gene, is shown in FIG. 1. The expression levels of cytochrome P450 716B1- like protein gene in high Rebaudioside M *Stevia* lines are significantly lower than that in high Stevioside *Stevia* lines, high Rebaudioside A *Stevia* lines and high Rebaudioside D *Stevia* lines. This cytochrome P450 enzyme could modify SG or SG precursors to reduce the metabolic flow towards SG biosynthesis. Mutations in this gene could reduce the undesired branching reaction, and could redirect metabolic flow toward more Reb M biosynthesis.

Many techniques for gene silencing are well-known to one of skill in the art, including, but not limited to, knock-outs (such as by insertion of a transposable element such as Mu (Vicki Chandler, *The Maize Handbook*, Ch. 118 (Springer-Verlag 1994)) or other genetic elements such as a FRT, Lox, or other site specific integration sites; antisense technology (see, e.g., Sheehy, et al., PNAS USA, 85:8805-8809 (1988) and U.S. Pat. Nos. 5,107,065, 5,453,566, and 5,759,829); co-suppression (e.g., Taylor, *Plant Cell*, 9:1245 (1997); Jorgensen, *Trends Biotech.*, 8(12):340-344 (1990); Flavell, PNAS USA, 91:3490-3496 (1994); Finnegan, et al., *Bio/Technology*, 12:883-888 (1994); Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); Montgomery, et al., *PNAS USA*, 95:15502-15507 (1998)), virus-induced gene silencing (Burton, et al., *Plant Cell*, 12:691-705 (2000); Baulcombe, *Curr. Op. Plant Bio.*, 2:109-113 (1999)); target-RNA-specific ribozymes (Haseloff, et al., *Nature*, 334:585-591 (1988)); hairpin structures (Smith, et al., *Nature*, 407:319-320 (2000); U.S. Pat. Nos. 6,423,885, 7,138,565, 6,753,139, and 7,713,715); MicroRNA (Aukerman & Sakai, *Plant Cell*, 15:2730-2741 (2003)); ribozymes (Steinecke, et al., EMBO J., 11:1525 (1992); Perriman, et al., *Antisense Res. Dev.*, 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); and other methods or combinations of the above methods known to those of skill in the art.

Mutation breeding is another method to disrupt one or more negative regulator genes in the rebaudioside A to rebaudioside M conversion pathway. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, ionizing radiation, such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm); chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates such as ethyl methanesulfonate, sulfones, lactones), sodium azide, hydroxylamine, nitrous acid, methylnitrilsourea, or acridines; TILLING (targeting induced local lesions in genomes), where mutation is induced by chemical mutagens and mutagenesis is accompanies by the isolation of chromosomal DNA from every mutated plant line or seed and screening of the population of the seed or plants is performed at the DNA level using advanced molecular techniques; zinc finger nucleases. Once a desired trait is observed through mutagenesis the trait may then be incorporated into existing germplasm by traditional breeding techniques. Details of mutation breeding can be found in Sikora, Per, et al., "Mutagenesis as a Tool in Plant Genetics, Functional Genomics, and Breeding" *International Journal of Plant Genomics*. 2011 (2011); 13 pages; Petilino, Joseph F. "Genome editing in plants via designed zinc finger nucleases" *In Vitro Cell Dev Biol Plant*. 51(1): pp. 1-8 (2015); and Daboussi, Fayza, et al. "Engineering Meganuclease for Precise Plant Genome Modification" in *Advances in New Technology for Targeted Modification of Plant Genomes*. Springer Science+Business. pp 21-38 (2015).

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the embodiments are intended to be within the scope of the embodiments.

Gene Editing Using CRISPR

Targeted gene editing can be done using CRISPR/Cas9 technology (Saunders & Joung, Nature Biotechnology, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol*. 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system. See for example, Zhang, B. et al., "Exploiting the CRISPR/Cas9 System for Targeted Genome Mutagenesis in *Petunia*" *Science Reports, Vol.* 6, February 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476.

Breeding with Molecular Markers

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses. Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing the plants of the instant application. See Vainstein, "Breeding for Ornamentals: Classical and Molecular Approaches," Kluwer Academic Publishers (2002).

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See for example, Fletcher, Richard S., et al., "QTL analysis of root morphology, flowering time, and yield reveals trade-offs in response to drought in *Brassica napus*" *Journal of Experimental Biology*. 66 (1): 245-256 (2014). QTL markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Methods for Detecting SNPs for Marker Assisted Breeding

In addition to the direct or indirect sequencing of the site, SNPs may also be detected by a variety of effective methods well known in the art including those disclosed in U.S. Pat. Nos. 5,468,613 and 5,217,863; 5,210,015; 5,876,930; 6,030,787 6,004,744; 6,013,431; 5,595,890; 5,762,876; 5,945,283; 5,468,613; 6,090,558; 5,800,944 and 5,616,464. In particular, polymorphisms in DNA sequences can be detected by hybridization to allele-specific oligonucleotide (ASO) probes as disclosed in U.S. Pat. Nos. 5,468,613 and 5,217,863. The nucleotide sequence of an ASO probe is designed to form either a perfectly matched hybrid or to contain a mismatched base pair at the site of the variable nucleotide residues. The distinction between a matched and a mismatched hybrid is based on differences in the thermal stability of the hybrids in the conditions used during hybridization or washing, differences in the stability of the hybrids analyzed by denaturing gradient electrophoresis or chemical cleavage at the site of the mismatch.

If a SNP creates or destroys a restriction endonuclease cleavage site, it will alter the size or profile of the DNA fragments that are generated by digestion with that restriction endonuclease. As such, plants that possess a variant sequence can be distinguished from those having the original sequence by restriction fragment analysis. SNPs that can be identified in this manner are termed "restriction fragment length polymorphisms" ("RFLPs"). RFLPs have been widely used in human and plant genetic analyses (Glassberg, UK Patent Application 2135774; Skolnick et al., *Cytogen. Cell Genet.* 32:58-67 (1982); Botstein et al., *Ann. J. Hum. Genet.* 32:314-331 (1980); Fischer et al., PCT Application WO 90/13668; Uhlen, PCT Application WO 90/11369.

An alternative method of determining SNPs is based on cleaved amplified polymorphic sequences (CAPS) (Konieczny, A. and F. M. Ausubel, *Plant J.* 4:403-410 (1993); Lyamichev et al., *Science* 260:778-783 (1993). A modified version of CAPs, known as dCAPs, is a technique for detection of Single Nucleotide Polymorphisms (SNPs). The dCAPS technique introduces or destroys a restriction enzyme recognition sites by using primers that containing one or more mismatches to the template DNA. The PCR product modified in this manner is then subjected to restriction enzyme digestion and the presence or absence of the SNP is determined by the resulting restriction pattern. This technique is useful for genotyping known mutations and genetic mapping of isolated DNAs (Neff M M, Neff J D, Chory J, Pepper A E. dCAPS, a simple technique for the genetic analysis of single nucleotide polymorphisms: experimental applications in *Arabidopsis thaliana* genetics. *Plant J.* 1998 May; 14(3):387-92).

SNPs can also be identified by single strand conformation polymorphism (SSCP) analysis. The SSCP technique is a method capable of identifying most sequence variations in a single strand of DNA, typically between 150 and 250 nucleotides in length (Elles, *Methods in Molecular Medicine: Molecular Diagnosis of Genetic Diseases*, Humana Press (1996); Orita et al., *Genomics* 5:874-879 (1989). Under denaturing conditions a single strand of DNA will adopt a conformation that is uniquely dependent on its sequence. This conformation usually will be different even if only a single base is changed. Most conformations have been reported to alter the physical configuration or size sufficiently to be detectable by electrophoresis. A number of protocols have been described for SSCP including, but not limited to Lee et al., *Anal. Biochem.* 205:289-293 (1992); Suzuki et al., *Anal. Biochem.* 192:82-84 (1991); Lo et al., *Nucleic Acids Research* 20:1005-1009 (1992); Sarkar et al., *Genomics* 13:441-443 (1992).

SNPs may also be detected using a DNA fingerprinting technique called amplified fragment length polymorphism (AFLP), which is based on the selective PCR amplification of restriction fragments from a total digest of genomic DNA to profile that DNA. Vos et al., *Nucleic Acids Res.* 23:4407-4414 (1995). This method allows for the specific co-amplification of many restriction fragments, which can be analyzed without knowledge of the nucleic acid sequence. AFLP employs basically three steps. Initially, a sample of genomic DNA is cut with restriction enzymes and oligonucleotide adapters are ligated to the restriction fragments of the DNA. The restriction fragments are then amplified using PCR by using the adapter and restriction sequence as target sites for primer annealing. The selective amplification is achieved by the use of primers that extend into the restriction fragments, amplifying only those fragments in which the primer extensions match the nucleotide flanking the restriction sites. These amplified fragments are then visualized on a denaturing polyacrylamide gel (Beismann et al., *Mol. Ecol.* 6:989-993 (1997); Janssen et al., *Int. J. Syst. Bacteriol*

47:1179-1187 (1997); Huys et al., *Int. J. Syst. Bacteriol.* 47:1165-1171 (1997); McCouch et al., *Plant Mol. Biol.* 35:89-99 (1997); Nandi et al., *Mol. Gen. Genet.* 255:1-8 (1997); Cho et al. *Genome* 39:373-378 (1996); Simons et al., *Genomics* 44:61-70 (1997); Cnops et al., *Mol. Gen. Genet.* 253:32-41 (1996); Thomas et al., *Plant J.* 8:785-794 (1995).

SNPs may also be detected using random amplified polymorphic DNA (RAPD) (Williams et al., *Nucl. Acids Res.* 18:6531-6535 (1990).

SNPs can be detected by methods as disclosed in U.S. Pat. Nos. 5,210,015; 5,876,930 and 6,030,787 in which an oligonucleotide probe having reporter and quencher molecules is hybridized to a target polynucleotide. The probe is degraded by 5'→3' exonuclease activity of a nucleic acid polymerase.

SNPs can also be detected by labelled base extension methods as disclosed in U.S. Pat. Nos. 6,004,744; 6,013, 431; 5,595,890; 5,762,876; and 5,945,283. These methods are based on primer extension and incorporation of detectable nucleoside triphosphates. The primer is designed to anneal to the sequence immediately adjacent to the variable nucleotide which can be can be detected after incorporation of as few as one labelled nucleoside triphosphate. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labelled sequence-specific oligonucleotide probe Other methods for identifying and detecting SNPs in addition to those described above include the use of restriction enzymes (Botstein et al., *Am. J. Hum. Genet.* 32:314-331 (1980); and Konieczny and Ausubel, *Plant J.* 4:403-410 (1993)), enzymatic and chemical mismatch assays (Myers et al., *Nature* 313:495-498 (1985)), allele-specific PCR (Newton et al., *Nucl. Acids Res.* 17:2503-2516 (1989); and Wu et al., *Proc. Natl. Acad. Sci. USA* 86:2757-2760 (1989)), ligase chain reaction (Barany, *Proc. Natl. Acad. Sci. USA* 88:189-193 (1991)), single-strand conformation polymorphism analysis (Labrune et al., *Am. J. Hum. Genet.* 48: 1115-1120 (1991)), single base primer extension (Kuppuswamy et al., *Proc. Natl. Acad. Sci. USA* 88:1143-1147 (1991); and Goelet, U.S. Pat. Nos. 6,004,744 and 5,888,819, solid-phase ELISA-based oligonucleotide ligation assays (Nikiforov et al., *Nucl. Acids Res.* 22:4167-4175 (1994)), dideoxy fingerprinting (Sarkar et al., *Genomics* 13:441-443 (1992)), oligonucleotide fluorescence-quenching assays (Livak et al., *PCR Methods Appl.* 4:357-362 (1995)), 5'-nuclease allele-specific hybridization TAQMAN assay (Livak et al., *Nature Genet.* 9:341-342 (1995)), template-directed dye-terminator incorporation (TDI) assay (Chen and Kwok, *Nucl. Acids Res.* 25:347-353 (1997)), allele-specific molecular beacon assay (Tyagi et al., *Nature Biotech.* 16: 49-53 (1998)), PinPoint assay (Haff and Smirnov, *Genome Res.* 7: 378-388 (1997)), dCAPS analysis (Neffetal., *Plant J.* 14:387-392 (1998)), pyrosequencing (Ronaghi et al, *Analytical Biochemistry* 267:65-71 (1999); Ronaghi et al PCT application WO 98/13523; and Nyren et al PCT application WO 98/28440), using mass spectrometry e.g., the MASSCODE system (Howbert et al WO 99/05319; Howber et al WO 97/27331), mass spectroscopy (U.S. Pat. No. 5,965,363, invasive cleavage of oligonucleotide probes (Lyamichev et al *Nature Biotechnology* 17:292-296), and using high density oligonucleotide arrays (Hacia et al *Nature Genetics* 22:164-167).

While certain methods for detecting SNPs are described herein, other detection methodologies may be utilized. For example, additional methodologies are known and set forth, in Birren et. al., *Genome Analysis*, 4:135-186, *A Laboratory Manual*. Mapping Genomes, Cold Spring Harbor Laboratory Press, Cold Spring Harbor, N.Y. (1999); Maliga et al., *Methods in Plant Molecular Biology. A Laboratory Course Manual*, Cold Spring Harbor Laboratory Press, Cold Spring Harbor, N.Y. (1995); Paterson, *Biotechnology Intelligence Unit: Genome Mapping in Plants*, R.G. Landes Co., Georgetown, Tex., and Academic Press, San Diego, Calif. (1996); *The Maize Handbook*, Freeling and Walbot, eds., Springer-Verlag, New York, N.Y. (1994); *Methods in Molecular Medicine: Molecular Diagnosis of Genetic Diseases*, Elles, ed., Humana Press, Totowa, N.J. (1996); Clark, ed., *Plant Molecular Biology: A Laboratory Manual*, Clark, ed., Springer-Verlag, Berlin, Germany (1997).

Methods for Detecting and Measuring Steviol Glycosides

Steviol glycosides may be detected and measured using HPLC. The protocol described below is an example.

For HPLC analysis, the *stevia* leaf samples were air-dried/oven-dried before grinding into fine powder using a pestle and mortar. For each sample, leaf powder (100 mg) was extracted with 15 ml of 60° C. distilled water for 18 hours. The mixture was centrifuged and the supernatant filtered and collected for steviol glycoside composition analysis by HPLC (Agilent, USA). The analysis of steviol glycosides was carried out using an Agilent Technologies 1200 Series (USA) HPLC equipped Agilent® Poroshell® 120 SB-C18 2.7 μm, 4.6×150 mm A diode array set at 210 nm was used as the detector. The reference standards for all glycosides, including rebaudioside E, RebD, RebM, rebaudioside N, and rebaudioside O were purchased from ChromaDex Inc. (USA). The following method was used for analysis of Rebaudioside E (RebE), RebD, RebM, Rebaudioside N (RebN), and Rebaudioside O (RebO): column temperature: 40° C., mobile phase: Solvent A 10 mM Monosodium dihydrogen Phosphate pH2.6: Acetonitrile, 75%:25% (v/v), Solvent B Water: Acetonitrile, 50%:50% (v/v), Gradient program % v/v: at 0.0 and 14.0 minutes 100% A and 0% B, at 14.5 and 25.0 minutes 100% B and 0% A, flow rate: 0.5 mL/min, injection: 5 μL, auto-sampler temperature: ambient. To analyze Rebaudioside A (RebA), Stevioside (Stev), Rebaudioside F (RebF), Rebaudioside C (RebC), Dulcoside A (DulA), Rubusoside (Rub), Rebaudioside B (RebB), and Steviolbioside (Stev) the same method as described above was used except the mobile phase consisted of Isocratic 10 mM Monosodium di-hydrogen Phosphate pH 2.6: Acetonitrile, 68%:32% (v/v) at a flow rate of 1.0 mL/min, with a run time of 20 minutes In addition to HPLC, steviol glycosides may be detected and measured by a number of methods well known in the art.

Additional Breeding Methods

There are numerous steps in the development of any desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single cultivar an improved combination of desirable traits from the parental germplasm. In *stevia*, the important traits leaf yield, earlier maturity, improved leaf quality, rebaudioside content, stevioside content, resistance to diseases and insects, resistance to drought and heat, and improved agronomic traits. Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to popular cultivars in environments representative of the commercial target area(s) for three or more years. The lines having superiority over the popular cultivars are candidates to become new commercial cultivars. Those lines still deficient in a few traits are discarded or utilized as parents to produce new populations for further selection.

These processes, which lead to the final step of marketing and distribution, usually take from seven to twelve years from the time the first cross is made. Therefore, development of new cultivars is a time-consuming process that requires precise forward planning, efficient use of resources, and a minimum of changes in direction.

A most difficult task is the identification of individuals that are genetically superior because for most traits the true genotypic value is masked by other confounding plant traits or environmental factors. One method of identifying a superior plant is to observe its performance relative to other experimental lines and widely grown standard cultivars. For many traits a single observation is inconclusive, and replicated observations over time and space are required to provide a good estimate of a line's genetic worth.

The goal of a commercial *stevia* breeding program is to develop new, unique, and superior *stevia* cultivars. The breeder initially selects and crosses two or more parental lines, followed by generation advancement and selection, thus producing many new genetic combinations. The breeder can theoretically generate billions of different genetic combinations via this procedure. The breeder has no direct control over which genetic combinations will arise in the limited population size which is grown. Therefore, two breeders will never develop the same line having the same traits.

Each year, the plant breeder selects the germplasm to advance to the next generation. This germplasm is grown under unique and different geographical, climatic, and soil conditions and further selections are then made, during and at the end of the growing season. The lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce, with any reasonable likelihood, the same cultivar twice by using the exact same original parents and the same selection techniques. This unpredictability results in the expenditure of large amounts of research moneys to develop superior new *stevia* cultivars.

Pureline cultivars of *stevia* are commonly bred by hybridization of two or more parents followed by selection. The complexity of inheritance, the breeding objectives, and the available resources influence the breeding method. Pedigree breeding, recurrent selection breeding, and backcross breeding are breeding methods commonly used in self-pollinated crops such as *stevia*. These methods refer to the manner in which breeding pools or populations are made in order to combine desirable traits from two or more cultivars or various broad-based sources. The procedures commonly used for selection of desirable individuals or populations of individuals are called mass selection, plant-to-row selection, and single seed descent or modified single seed descent. One or a combination of these selection methods can be used in the development of a cultivar from a breeding population.

Pedigree breeding is primarily used to combine favorable genes into a totally new cultivar that is different in many traits than either parent used in the original cross. It is commonly used for the improvement of self-pollinating crops. Two parents which possess favorable, complementary traits are crossed to produce an $F_1$ (filial generation 1). An $F_2$ population is produced by selfing $F_2$ plants. Selection of desirable individual plants may begin as early as the $F_2$ generation wherein maximum gene segregation occurs. Individual plant selection can occur for one or more generations. Successively, seed from each selected plant can be planted in individual, identified rows or hills, known as progeny rows or progeny hills, to evaluate the line and to increase the seed quantity, or to further select individual plants. Once a progeny row or progeny hill is selected as having desirable traits, it becomes what is known as a breeding line that is specifically identifiable from other breeding lines that were derived from the same original population. At an advanced generation (i.e., $F_5$ or higher) seed of individual lines are evaluated in replicated testing. At an advanced stage the best lines or a mixture of phenotypically similar lines from the same original cross are tested for potential release as new cultivars.

The single seed descent procedure in the strict sense refers to planting a segregating population, harvesting one seed from every plant, and combining these seeds into a bulk, which is planted as the next generation. When the population has been advanced to the desired level of inbreeding, the plants from which lines are derived will each trace to different $F_2$ individuals. Primary advantages of the seed descent procedures are to delay selection until a high level of homozygosity (e.g., lack of gene segregation) is achieved in individual plants, and to move through these early generations quickly, usually through using winter nurseries.

The modified single seed descent procedures involve harvesting multiple seed (i.e., a single lock or a simple boll) from each plant in a population and combining them to form a bulk. Part of the bulk is used to plant the next generation and part is put in reserve. This procedure has been used to save labor at harvest and to maintain adequate seed quantities of the population.

Selection for desirable traits can occur at any segregating generation ($F_2$ and above). Selection pressure is exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

Methods to Determine the Genotype of *Stevia*

In addition to phenotypic observations, the genotype of a plant can also be examined. There are many laboratory-based techniques available for the analysis, comparison, and characterization of plant genotype. Among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max* L. Merr.) pp. 6.131-6.138 in S. J. O'Brien (Ed.) *Genetic Maps: Locus Maps of Complex Genomes*, Cold Spring Harbor Laboratory Press, Cold Spring Harbor, N.Y., (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (Eds.), *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.*, 95:22-225 (1997). Additional SNPs to those described herein may also be used to identify the unique genetic composition of the invention and progeny varieties retaining that unique genetic composition. Various molecular marker techniques may be used in combination to enhance overall resolution.

Molecular markers, which includes markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. For example, molecular markers are used in soybean breeding for selection of the trait of resistance to soybean cyst nematode, see U.S. Pat. No. 6,162,967. The markers can also be used to select toward the genome of the recurrent parent and against the markers of the donor parent. Using this procedure can attempt to minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection. Molecular markers may also be used to identify and exclude certain sources of germplasm as parental varieties or ancestors of a plant by providing a means of tracking genetic profiles through crosses as discussed more fully hereinafter.

Further Embodiments

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed, in particular embodiments, also relates to transformed versions of the claimed cultivar.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed *stevia* plants, using transformation methods as described below to incorporate transgenes into the genetic material of the *stevia* plant(s).

Expression Vectors for *Stevia* Transformation: Marker Genes

Expression vectors include at least one genetic marker operably linked to a regulatory element (for example, a promoter) that allows transformed cells containing the marker to be either recovered by negative selection (i e, inhibiting growth of cells that do not contain the selectable marker gene), or by positive selection (i.e., screening for the product encoded by the genetic marker). Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII), which, when under the control of plant regulatory signals, confers resistance to kanamycin. Fraley, et al., *PNAS*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate, or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Other selectable marker genes for plant transformation that are not of bacterial origin include, for example, mouse dihydrofolate reductase, plant 5-enolpyruvyl-shikimate-3-phosphate synthase and plant acetolactate synthase. Eichholtz, et al., *Somatic Cell Mol. Genet.*, 13:67 (1987); Shah, et al., *Science*, 233:478 (1986); Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase. Jefferson, R. A., *Plant Mol. Biol. Rep.*, 5:387 (1987); Teeri, et al., *EMBO J.*, 8:343 (1989); Koncz, et al., *PNAS*, 84:131 (1987); DeBlock, et al., *EMBO J.* 3:1681 (1984).

In-vivo methods for visualizing GUS activity that do not require destruction of plant tissue are available. Molecular Probes Publication 2908, IMAGENE GREEN, pp. 1-4 (1993) and Naleway, et al., *J. Cell Biol.*, 115:151a (1991). However, these in-vivo methods for visualizing GUS activity have not proven useful for recovery of transformed cells because of low sensitivity, high fluorescent backgrounds, and limitations associated with the use of luciferase genes as selectable markers. A gene encoding Green Fluorescent Protein (GFP) has been utilized as a marker for gene expression in prokaryotic and eukaryotic cells. Chalfie, et al., *Science*, 263:802 (1994). GFP and mutants of GFP may be used as screenable markers.

Expression Vectors for *Stevia* Transformation: Promoters

Genes included in expression vectors must be driven by a nucleotide sequence comprising a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in *stevia*. Optionally, the inducible promoter is operably linked to a nucleotide sequence encoding a signal sequence which is operably linked to a gene for expression in *stevia*. With an inducible promoter the rate of transcription increases in response to an inducing agent.

Any inducible promoter can be used in the instant invention. See Ward, et al., *Plant Mol. Biol.,* 22:361-366 (1993). Exemplary inducible promoters include, but are not limited to, that from the ACEI system which responds to copper (Mett, et al., *PNAS,* 90:4567-4571 (1993)); In2 gene from maize which responds to benzenesulfonamide herbicide safeners (Hershey, et al., *Mol. Gen. Genet.,* 227:229-237 (1991) and Gatz, et al., *Mol. Gen. Genet.,* 243:32-38 (1994)); or Tet repressor from Tn10 (Gatz, et al., *Mol. Gen. Genet.,* 227:229-237 (1991)). An example inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena, et al., *PNAS,* 88:0421 (1991)).

B. Constitutive Promoters:

A constitutive promoter is operably linked to a gene for expression in *stevia* or the constitutive promoter is operably linked to a nucleotide sequence encoding a signal sequence which is operably linked to a gene for expression in *stevia*.

Many different constitutive promoters can be utilized in the instant invention. Exemplary constitutive promoters include, but are not limited to, the promoters from plant viruses such as the 35S promoter from CaMV (Odell, et al., *Nature,* 313:810-812 (1985)) and the promoters from such genes as rice actin (McElroy, et al., *Plant Cell,* 2:163-171 (1990)); ubiquitin (Christensen, et al., *Plant Mol. Biol.,* 12:619-632 (1989) and Christensen, et al., *Plant Mol. Biol.,* 18:675-689 (1992)); pEMU (Last, et al., *Theor. Appl. Genet.,* 81:581-588 (1991)); MAS (Velten, et al., *EMBO J.,* 3:2723-2730 (1984)); and maize H3 histone (Lepetit, et al., *Mol. Gen. Genet.,* 231:276-285 (1992) and Atanassova, et al., *Plant Journal,* 2 (3): 291-300 (1992)).

The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT Application No. WO 96/30530.

C. Tissue-Specific or Tissue-Preferred Promoters:

A tissue-specific promoter is operably linked to a gene for expression in *stevia*. Optionally, the tissue-specific promoter is operably linked to a nucleotide sequence encoding a signal sequence which is operably linked to a gene for expression in *stevia*. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., *Science,* 23:476-482 (1983) and Sengupta-Gopalan, et al., *PNAS,* 82:3320-3324 (1985)); a leaf-specific and light-induced promoter, such as that from cab or rubisco (Simpson, et al., *EMBO J.,* 4(11):2723-2729 (1985) and Timko, et al., *Nature,* 318:579-582 (1985)); an anther-specific promoter, such as that from LAT52 (Twell, et al., *Mol. Gen. Genet.,* 217:240-245 (1989)); a pollen-specific promoter, such as that from Zm13 (Guerrero, et al., *Mol. Gen. Genet.,* 244:161-168 (1993)); or a microspore-preferred promoter, such as that from apg (Twell, et al., *Sex. Plant Reprod.,* 6:217-224 (1993)).

Signal Sequences for Targeting Proteins to Subcellular Compartments

Transport of protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.,* 20:49 (1992); Close, P. S., Master's Thesis, Iowa State University (1993); Knox, C., et al., *Plant Mol. Biol.,* 9:3-17 (1987); Lerner, et al., *Plant Physiol.,* 91:124-129 (1989); Fontes, et al., *Plant Cell,* 3:483-496 (1991); Matsuoka, et al., *PNAS,* 88:834 (1991); Gould, et al., *J. Cell. Biol.,* 108:1657 (1989); Creissen, et al., *Plant J.,* 2:129 (1991); Kalderon, et al., *Cell,* 39:499-509 (1984); Steifel, et al., *Plant Cell,* 2:785-793 (1990).

Methods for *Stevia* Transformation

Numerous methods for plant transformation have been developed, including biological and physical, plant transformation protocols. See, for example, Mild, et al., "Procedures for Introducing Foreign DNA into Plants" in *Methods in Plant Molecular Biology and Biotechnology,* Glick and Thompson (Eds.), CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology,* Glick and Thompson (Eds.), CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., *Science,* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci., 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.,* 8:238 (1989). See also, U.S. Pat. No. 5,563,055 (Townsend and Thomas), issued Oct. 8, 1996.

B. Direct Gene Transfer:

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 μm to 4 μm. The expression vector is introduced into plant tissues with a biolistic device that accelerates the microprojectiles to speeds of 300 m/s to 600 m/s which is sufficient to penetrate plant cell walls and membranes. Sanford, et al., *Part. Sci. Technol.,* 5:27 (1987); Sanford, J. C., *Trends Biotech.,* 6:299 (1988); Klein, et al., *Bio/technology,* 6:559-563 (1988); Sanford, J. C., *Physiol Plant,* 7:206 (1990); Klein, et al., *Bio/technology,* 10:268 (1992). See also, U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang, et al., *Bio/technology,* 9:996 (1991). Alternatively, liposome and spheroplast fusion have been used to introduce expression vectors into plants. Deshayes, et al., *EMBO J.,* 4:2731 (1985); Christou, et al., *PNAS,* 84:3962 (1987). Direct uptake of DNA into protoplasts using $CaCl_2$) precipitation, polyvinyl alcohol, or poly-L-ornithine has also been reported. Hain, et al., *Mol. Gen. Genet.,* 199:161 (1985) and Draper, et al., *Plant Cell Physiol.* 23:451 (1982). Electroporation of protoplasts and whole cells and tissues has also been described. Donn, et al., In Abstracts of VIIth International Congress on Plant Cell and Tissue Culture IAPTC, A2-38, p. 53 (1990); D'Halluin, et al., *Plant Cell,* 4:1495-1505 (1992); and Spencer, et al., *Plant Mol. Biol.,* 24:51-61 (1994).

Following transformation of *stevia* target tissues, expression of the above-described selectable marker genes allows for preferential selection of transformed cells, tissues, and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular *stevia* cultivar using the foregoing transformation techniques could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

C. Single-Gene Conversion

When the term "*stevia* plant" is used herein, this also includes any single gene conversions of that variety. The term "single gene converted plant" as used herein refers to those *stevia* plants which are developed by a plant breeding technique called backcrossing wherein essentially all of the desired morphological and physiological characteristics of a variety are recovered in addition to the single gene transferred into the variety via the backcrossing technique. Backcrossing methods can be used herein to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental *stevia* plant which contributes the gene for the desired characteristic is termed the "nonrecurrent" or "donor parent". This terminology refers to the fact that the nonrecurrent parent is used one time in the backcross protocol and therefore does not recur. The parental *stevia* plant to which the gene or genes from the nonrecurrent parent are transferred is known as the recurrent parent as it is used for several rounds in the backcrossing protocol (Poehlman & Sleper (1994); Fehr (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a *stevia* plant is obtained wherein essentially all of the desired morphological and physiological characteristics of the recurrent parent are recovered in the converted plant, in addition to the single transferred gene from the nonrecurrent parent, as determined at the 5% significance level when grown in the same environmental conditions.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic. Examples of these traits include but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus. Several of these single gene traits are described in U.S. Pat. Nos. 5,959,185; 5,973,234; and 5,977,445, the disclosures of which are specifically hereby incorporated by reference.

Further reproduction of the variety can occur by tissue culture and regeneration. Tissue culture of various tissues of *stevia* and regeneration of plants therefrom is well known and widely published. For example, reference may be had to Komatsuda, T., et al., *Crop Sci.,* 31:333-337 (1991); Stephens, P. A., et al., *Theor. Appl. Genet.,* 82:633-635 (1991); Komatsuda, T., et al., *Plant Cell, Tissue and Organ Culture,* 28:103-113 (1992); Dhir, S., et al. *Plant Cell Rep.,* 11:285-289 (1992); Pandey, P., et al., *Japan J. Breed.,* 42:1-5 (1992); and Shetty, K., et al., *Plant Science,* 81:245-251 (1992); as well as U.S. Pat. No. 5,024,944 issued Jun. 18, 1991 to Collins, et al., and U.S. Pat. No. 5,008,200 issued Apr. 16, 1991 to Ranch, et al. Thus, another aspect of this invention is to provide cells which upon growth and differentiation produce *stevia* plants having high RebD and RebM as well as the markers SNPs disclosed herein.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185; 5,973,234; and U.S. Pat. No. 5,977,445, described certain techniques.

Methods for Extraction and Purification of Glycosides

Methods for the extraction and purification of sweet glycosides from the *Stevia rebaudiana* plant using water or organic solvents are described in, for example, U.S. Pat. Nos. 4,361,697; 4,082,858; 4,892,938; 5,972,120; 5,962,678; 7,838,044 and 7,862,845. Processes for the extraction of RebD are described in U.S. Pat. No. 9,029,426, and the extraction of RebM are provided in U.S. application Ser. No. 14/254,653.

The compositions can be used as sweetness enhancers, flavor enhancers and sweeteners in various food and beverage products. Examples of food and beverage products include, but are not limited to, carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables. Additionally the compositions can be used in drug or pharmaceutical preparations and cosmetics, including but not limited to toothpaste, mouthwash, cough syrup, chewable tablets, lozenges, vitamin preparations, and the like. The compositions can be used "as-is" or in combination with other sweeteners, flavors and food ingredients.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions, and sub-combinations as are within their true spirit and scope.

One or more aspects may be embodied in other specific forms without departing from its spirit or essential characteristics. The described embodiments are to be considered in all respects only as illustrative and not restrictive. The scope of the embodiments is, therefore, indicated by the appended claims rather than by the foregoing description. All changes which come within the meaning and range of equivalency of the claims are to be embraced within their scope.

The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the claimed embodiments require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice one or more embodiments.

While a number of exemplary aspects and embodiments have been discussed above, those of skill in the art will recognize certain modifications, permutations, additions, and sub-combinations thereof. It is therefore intended that the following appended claims and claims hereafter are interpreted to include all such modifications, permutations, additions, and sub-combinations as are within their true spirit and scope.

What is claimed is:

1. A *Stevia rebaudiana* plant comprising at least one disrupted negative regulator gene in the rebaudioside A to rebaudioside M conversion pathway, and wherein the negative regulator gene is selected from the group consisting of SEQ ID NO:9 and SEQ ID NO:10.

2. A method of increasing the rebaudioside M content in a *Stevia rebaudiana* plant by inducing a disruption in at least one negative regulator gene function in the plant, wherein said negative regulator gene is selected from the group consisting of SEQ ID NO:9 and SEQ ID NO:10.

3. A plant part of the *Stevia rebaudiana* plant of claim 1, wherein the plant part is selected from the group consisting of leaves, pollen, embryos, cotyledons, hypocotyl, meristematic cells, ovules, seeds, cells, roots, root tips, pistils, anthers, flowers, and stems.

4. A plant, plant part, or cell produced by the method of claim 2, comprising in its genome or more genes affecting metabolism and selected from the group consisting of SEQ ID NO:9 and SEQ ID NO:10.

5. A method of producing a *Stevia* plant comprising the steps of:

a) introducing a recombinant DNA construct comprising a nucleotide sequence comprising one or more sequences selected from the group consisting of SEQ ID NO:9 and SEQ ID NO:10 operably linked to at least one heterologous nucleotide sequence into a *Stevia rebaudiana* plant, wherein said heterologous nucleotide sequence is a promoter;

b) growing a fertile, mature plant resulting from step a); and c) selecting a plant expressing the at least one heterologous nucleotide sequence in at least one plant tissue.

* * * * *